(12) United States Patent
Snoeck

(10) Patent No.: US 6,544,979 B1
(45) Date of Patent: Apr. 8, 2003

(54) FUSED IMIDAZOLE DERIVATIVES FOR IMPROVING ORAL BIOAVAILABILITY OF PHARMACEUTICAL AGENTS

(75) Inventor: Henricus Johannes Matheus Snoeck, Meerhout (BE)

(73) Assignee: Janssen Pharmaceuticals, N.V. (BE)

( * ) Notice: Subject to any disclaimer, the term of this patent is extended or adjusted under 35 U.S.C. 154(b) by 0 days.

(21) Appl. No.: 09/508,748

(22) PCT Filed: Sep. 10, 1998

(86) PCT No.: PCT/EP98/05751

§ 371 (c)(1),
(2), (4) Date: Mar. 15, 2000

(87) PCT Pub. No.: WO99/13871

PCT Pub. Date: Mar. 25, 1995

(30) Foreign Application Priority Data

Sep. 18, 1997 (EP) .............................................. 97202862

(51) Int. Cl.$^7$ .................... C07D 471/04; C07D 487/04; A61K 31/435; A61K 31/55; A61K 31/553
(52) U.S. Cl. .............................. 514/211.1; 514/214.02; 514/292; 514/293; 540/548; 540/578; 540/579; 546/82; 546/83; 546/84
(58) Field of Search ........................ 514/211.1, 214.02, 514/292, 293; 540/548, 578, 579; 546/82, 83, 84

(56) References Cited

U.S. PATENT DOCUMENTS 6,218,381 B1 * 4/2001 Janssens et al. ......... 514/211.1

FOREIGN PATENT DOCUMENTS

| EP | 0 518 434 A1 | 12/1992 |
|---|---|---|
| EP | 0 518 435 A1 | 12/1992 |
| WO | WO 94/13680 A1 | 6/1994 |
| WO | WO 97/24356 A1 | 7/1997 |
| WO | WO 97/34897 A1 | 9/1997 |

OTHER PUBLICATIONS

Silverman, J.A., Pharm. Biotechnol., 12, 1999, 353–86, cited in Medline abstract only.*
International Publication No. WO 99/13871 –Search Report published Jun. 3, 1999.

* cited by examiner

Primary Examiner—Mukund J. Shah
Assistant Examiner—Thomas McKenzie

(57) ABSTRACT

This invention concerns the use of compounds of formula

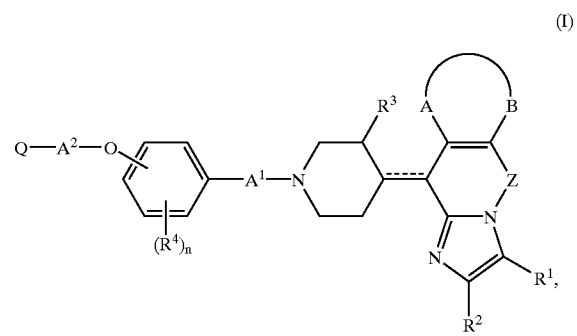

(I)

the N-oxide forms, the pharmaceutically acceptable addition salts and the stereochemically isomeric forms thereof, wherein the dotted line is an optional bond; n is 1 or 2; $R^1$ is hydrogen; halo; formyl; $C_{1-4}$alkyl optionally substituted with hydroxy, $C_{1-4}$alkyloxy, $C_{1-4}$alkylcarbonyloxy, imidazolyl, thiazolyl or oxazolyl; or a radical of formula —X—COOR$^5$, —X—CONR$^6$R$^7$ or —X—COR$^{10}$ wherein —X—is a direct bond, $C_{1-4}$alkanediyl or $C_{2-6}$alkenediyl; $R^5$ is hydrogen, $C_{1-12}$alkyl, Ar, Het, $C_{1-6}$alkyl substituted with $C_{1-4}$alkyloxy, aryl or heteroaryl; $R^6$ and $R^7$ each independently are hydrogen or $C_{1-4}$alkyl; $R^2$ is hydrogen, halo, $C_{1-4}$alkyl, hydroxy$C_{1-4}$alkyl, $C_{1-4}$alkyloxycarbonyl, carboxyl, formyl or phenyl; $R^3$ is hydrogen, $C_{1-4}$alkyl or $C_{1-4}$alkyloxy; $R^4$ is hydrogen, halo, $C_{1-4}$alkyl, $C_{1-4}$alkyloxy or halo$C_{1-4}$alkyl; Z is —CH$_2$—, —CH$_2$—CH$_2$—, —CH═CH—, —CHOH—CH$_2$—, —O—CH$_2$—, 13 C(═O)—CH$_2$—or —C(═NOH)—CH$_2$—; —A—B—is a bivalent radical; A$^1$ is a direct bond, optionally substituted $C_{1-6}$alkanediyl, $C_{1-6}$alkanediyl-oxy-$C_{1-6}$alkanediyl, carbonyl, $C_{1-6}$alkanediylcarbonyl, optionally substituted $C_{1-6}$alkanediyloxy; A$^2$ is a direct bond or $C_{1-6}$alkanediyl; and Q is aryl; for the manufacture of a medicine for improving the bioavailability of a second pharmaceutical agent which is co-administered orally to a warm-blooded animal.

10 Claims, No Drawings

FUSED IMIDAZOLE DERIVATIVES FOR IMPROVING ORAL BIOAVAILABILITY OF PHARMACEUTICAL AGENTS

This application is a National Stage application under 35 U.S.C. 371 of PCT/EP98/05751 filed Sep. 10, 1998, which claims priority from EP 97.202.862.5, filed Sep. 18, 1997.

This invention relates to fused imidazole derivatives having multidrug resistance modulating properties, and their use for improving oral bioavailability of pharmaceutical agents that are poorly absorbed from the gastrointestinal tract.

Many valuable pharmaceutical agents cannot be effectively administered by the oral route because of poor systemic absorption from the gastrointestinal tract. All these pharmaceutical agents are, therefore, generally administered via intravenous or intramuscular routes, requiring intervention by a physician or other health care professional, entailing considerable discomfort and potential local trauma to the patient and even requiring administration in a hospital setting with surgical access in the case of certain iv infusions.

It has been suggested that, in some cases, the poor bioavailability of pharmaceutical agents after oral administration is a result of the activity of a cell surface protein P-glycoprotein P-gp, which acts as an energy-dependent transport or efflux pump to decrease intracellular accumulation of said agent by extruding it from the cell. This P-glycoprotein has been identified in secretory epithelial cells of the liver, pancreas, small intestine, colon, and kidney; endothelial capillary cells of the brain and testis, placental trophoblasts; and the adrenal gland.

It is believed that the P-glycoprotein efflux pump prevents certain pharmaceutical compounds from transversing the mucosal cells of the small intestine and, therefore, from being absorbed into the systemic circulation.

Furthermore, it is believed that a major cause of multidrug resistance (MDR) is overexpression of the mdr-1 gene which codes for the expression of P-glycoprotein. P-glycoprotein decreases the intracellular concentration of cytotoxic drugs by binding the drug and actively pumping it out of the cell before it reaches a critical cytotoxic concentration (Dalton W. S., *Seminars in oncology,* 20:66–69, 1993). The term multidrug resistance (MDR) describes the phenomenon by which cells, in particular cancer cells, become resistant to multiple drugs that may have little similarity in the structure or mechanism of action.

Therefore, it has been suggested that compounds that are able to decrease, avoid, eliminate, inhibit or reverse the effects of multidrug resistance (i.e. so-called MDR reversing agents or compounds having MDR reversing properties) exert their action by blocking, inhibiting or suppressing the function of the P-glycoprotein efflux pump.

Since it is believed that the presence of P-glycoprotein in the gut epithelium can limit the uptake of certain orally administered pharmaceutical agents from the intestine, it is suggested that MDR inhibitors would be very useful to improve the bioavailability of orally administered pharmaceutical agents which are themselves poorly absorbed or not absorbed at all from the gastrointestinal tract.

EP-0,518,435 and EP-0,518,434, published on Dec. 16 1992, disclose fused imidazole compounds having antiallergic activity. WO-94/13680 published Jun. 23, 1994, discloses substituted imidazo[1,2-a](pyrrolo, thieno and furano) [2,3-d]azepine derivatives having antiallergic activity. Also WO-95/02600, published on Jan. 26 1995, discloses other piperidinyl- or piperidinylidene substituted imidazoazepine derivatives having antiallergic activity.

WO-93/16044, published on Aug. 19, 1993, discloses triphenyl-azacycloalkane derivatives effective in reversing drug resistance in multi-drug resistant tumors. WO-94/22842, published on Oct. 13, 1994, encompasses 1-amino-3-phenoxy propane derivatives as modulators of multi-drug resistance.

WO-97/34897, published on Sep. 25, 1997, discloses the fused imidazole derivatives of formula (I) as multidrug resistance modulators.

The compounds of the present invention differ from the cited art-known compounds structurally, by the nature of the substituents on the nitrogen of the piperidine moiety, and pharmacologically by the fact that, unexpectedly, these compounds have MDR modulating properties.

The present invention relates to the use of a first pharmaceutical compound of formula (I) for the manufacture of a medicine to improve the oral bioavailability of a second pharmaceutical agent that is poorly absorbed or not absorbed at all from the gastrointestinal tract or gut by pre-administering and/or simultaneously co-administering a first pharmaceutical compound of formula (I) to a warm-blooded animal by the oral route.

The phrases "oral bioavailability" and "bioavailability upon oral co-administration" as used herein refer to the systemic availability (i.e. blood/plasma levels) of a given amount of a pharmaceutical agent administered orally to a warm-blooded animal, in particular a human.

This invention concerns the use of a first pharmaceutical compound of formula

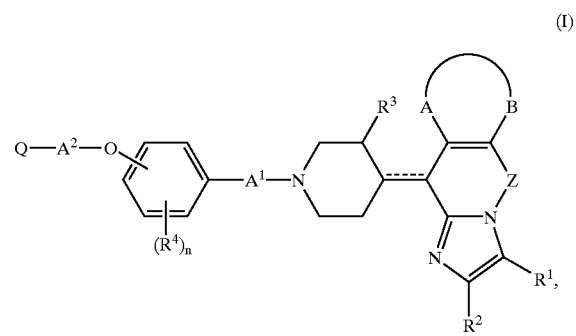

(I)

the N-oxide forms, the pharmaceutically acceptable addition salts and the stereo-chemically isomeric forms thereof, wherein the dotted line represents an optional bond;

n is 1 or 2;

$R^1$ is hydrogen; halo; formyl; $C_{1-4}$alkyl; $C_{1-4}$alkyl substituted with 1 or 2 substituents each independently selected from hydroxy, $C_{1-4}$alkyloxy, $C_{1-4}$alkylcarbonyloxy, imidazolyl, thiazolyl or oxazolyl; or a radical of formula

—X—CO—OR$^5$     (a-1);

—X—CO—NR$^6$R$^7$     (a-2);

or

—X—CO—R$^{10}$     (a-3);

wherein

—X— is a direct bond, $C_{1-4}$alkanediyl or $C_{2-6}$alkenediyl;

$R^5$ is hydrogen; $C_{1-12}$alkyl; Ar; Het; $C_{1-6}$alkyl substituted with $C_{1-4}$alkyloxy, $C_{1-4}$alkyloxycarbonyl$C_{1-4}$alkyloxy, Ar or Het;

$R^6$ and $R^7$ each independently are hydrogen or $C_{1-4}$alkyl;

$R^{10}$ is imidazolyl, thiazolyl or oxazolyl;

$R^2$ is hydrogen, halo, $C_{1-4}$alkyl, hydroxy$C_{1-4}$alkyl, $C_{1-4}$alkyloxycarbonyl, carboxyl, formyl or phenyl;

$R^3$ is hydrogen, $C_{1-4}$alkyl or $C_{1-4}$alkyloxy;

$R^4$ is hydrogen, halo, $C_{1-4}$alkyl, $C_{1-4}$alkyloxy or halo$C_{1-4}$alkyl;

Z is $Z^1$ or $Z^2$;

wherein $Z^1$ is a bivalent radical of formula —$CH_2$—, —$CH_2$—$CH_2$—or —CH=CH—; provided that when the dotted line is a bond, then $Z^1$ is other than —$CH_2$—;

$Z^2$ is a bivalent radical of formula —CHOH—$CH_2$—, —O—$CH_2$—, —C(=O)—$CH_2$— or —C(=NOH)—$CH_2$—;

—A—B— is a bivalent radical of formula

| | |
|---|---|
| —Y—$CR^8$=CH— | (c-1); |
| —CH=$CR^8$—Y— | (c-2); |
| —CH=$CR^8$—CH=CH— | (c-3); |
| —CH=CH—$CR^8$=CH— | (c-4); | or

| | |
|---|---|
| —CH=CH—CH=$CR^8$— | (c-5); | wherein each $R^8$ independently is hydrogen, halo, $C_{1-4}$alkyl, $C_{1-4}$alkyloxy, hydroxy$C_{1-4}$alkyl, hydroxycarbonyl$C_{1-4}$alkyl, formyl, carboxyl, ethenyl substituted with carboxyl, or ethenyl substituted with $C_{1-4}$alkyloxycarbonyl;

each Y dependently is a bivalent radical of formula —O—, —S— or —$NR^9$—; wherein $R^9$ is hydrogen, $C_{1-4}$alkyl or $C_{1-4}$alkylcarbonyl;

—$A^1$— is a direct bond; $C_{1-6}$alkanediyl; $C_{1-6}$alkanediyl-oxy-$C_{1-6}$alkanediyl; $C_{1-6}$alkanediyloxy; carbonyl; $C_{1-6}$alkanediylcarbonyl; $C_{1-6}$alkanediyloxy substituted with hydroxy;,or $C_{1-6}$alkanediyl substituted with hydroxy or =NOH;

—$A^2$— is a direct bond or $C_{1-6}$alkanediyl;

Q is phenyl; phenyl substituted with one or two substituents selected from hydrogen, halo, hydroxy, $C_{1-4}$alkyl, $C_{1-4}$alkyloxy or halo$C_{1-4}$alkyl; naphthalenyl; naphthalenyl substituted with one or two substituents selected from hydrogen, halo, hydroxy, $C_{1-4}$alkyl, $C_{1-4}$alkyloxy or halo$C_{1-4}$alkyl; pyridinyl; pyridinyl substituted with one or two substituents selected from hydrogen, halo, hydroxy, $C_{1-4}$alkyl, $C_{1-4}$alkyloxy or halo$C_{1-4}$alkyl; quinolinyl; or quinolinyl substituted with one or two substituents selected from;hydrogen, halo, hydroxy, $C_{1-4}$alkyl, $C_{1-4}$alkyloxy or halo$C_{1-4}$alkyl;

Ar is phenyl or phenyl substituted with 1, 2 or 3 substituents each independently selected from hydrogen, halo, $C_{1-4}$alkyl or $C_{1-4}$alkyloxy;

Het is furanyl; furanyl substituted with $C_{1-4}$alkyl, $C_{1-4}$alkyloxy or hydroxy$C_{1-4}$alkyl; oxazolyl; oxazolyl substituted with $C_{1-4}$alkyl or $C_{1-4}$alkyloxy; or quinolinyl; for the manufacture of a medicine for improving the bioavailability of a second pharmaceutical agent which is co-administered orally to a warm-blooded animal.

As used in the foregoing definitions and hereinafter, halo is generic to fluoro, chloro, bromo and iodo, $C_{1-4}$alkyl defines straight and branched chain saturated hydrocarbon radicals having from 1 to 4 carbon atoms such as, for example, methyl, ethyl, propyl, butyl, 1-methylethyl, 2-methylpropyl, 2,2-dimethylethyl and the like; $C_{1-6}$alkyl includes $C_{1-4}$alkyl and the higher homologues thereof having from 5 to 6 carbon atoms such as, for example, pentyl, hexyl, 3-methylbutyl, 2-methylpentyl and the like; $C_{1-12}$alkyl includes $C_{1-6}$alkyl and the higher homologues thereof having from 7 to 12 carbon atoms such as, for example, heptyl, octyl, nonyl, decyl and the like; $C_{1-4}$alkanediyl defines bivalent straight and branched chain saturated hydrocarbon radicals having from 1 to 4 carbon atoms such as, for example, methylene, 1,2-ethanediol, 1,3-propanediyl, 1,4-butanediyl and the like; $C_{1-5}$alkanediyl includes $C_{1-4}$alkanediyl and the higher homologues thereof having 5 carbon atoms such as, for example, 1,5-pentanediyl and the like; $C_{1-6}$alkanediyl includes $C_{1-5}$alkanediyl and the higher homologues thereof having 6 carbon atoms such as, for example, 1,6-hexanediyl and the like; $C_{2-6}$alkenyl defines straight and branched chain hydrocarbon radicals containing one double bond and having from 2 to 6 carbon atoms such as, for example, ethenyl, 2-propenyl, 3-butenyl, 2-pentenyl, 3-pentenyl, 3-methyl-2-butenyl, and the like; $C_{2-6}$alkenediyl defines straight and branched chain hydrocarbon radicals containing one double bond and having from 2 to 6 carbon atoms such as, for example, ethanediol, 2-propenediyl, 3-butenediyl, 2-pentenediyl, 3-pentenediyl, 3-methyl-2-butenediyl, and the like; halo-$C_{1-4}$alkyl is defined as mono- or polyhalosubstituted $C_{1-4}$alkyl; $C_{1-6}$alkanediyl-oxy-$C_{1-6}$alkanediyl defines bivalent radicals of formula such as, for example, —$CH_2$—$CH_2$—O—$CH_2$—$CH_2$—, —$CH_2$—CH($CH_2CH_3$)—O—CH($CH_3$)—$CH_2$—, —CH($CH_3$)—O—$CH_2$— and the like.

Whenever the bivalent radical $A^1$ is defined as a $C_{1-6}$alkanediylcarbonyl or $C_{1-6}$alkanediyloxy, preferably the $C_{1-6}$alkanediyl part of said radicals is connected to the nitrogen atom of the piperidine ring.

Pyridinyl and quinolinyl in the definition of Q are preferably connected to $A^2$ by a carbon atom.

Whenever Z is defined as $Z^2$, the —$CH_2$— moiety of said bivalent radical is preferably connected to the nitrogen of the imidazole ring.

Wherever $R^1$ or $R^{10}$ is defined as imidazolyl, thiazolyl or oxazolyl, said substituents are preferably connected by a carbon atom to the rest of the molecule.

The compounds where Z is —$CH_2$— and the optional bond is present are excluded by proviso because the tricyclic moiety in such compounds spontaneously aromatizes, thereby losing its multidrug resistance modulating properties.

The pharmaceutically acceptable addition salts as mentioned hereinabove are meant to comprise the therapeutically active non-toxic acid addition salt forms which the compounds of formula (I) are able to form. The latter can conveniently be obtained by treating the base form with such appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The pharmaceutically acceptable addition salts as mentioned hereinabove are meant to comprise the therapeutically active non-toxic base addition salt forms which the compounds of formula (I) are able to form. Examples of such base addition salt forms are, for example, the sodium, potassium, calcium salts, and also the salts with pharmaceutically. acceptable amines such as, for example, ammonia, alkylamines, benzathine, N-methyl-D-glucamine, hydrabamine, amino acids, e.g. arginine, lysine.

Conversely said salt forms can be converted by treatment with an appropriate base or acid into the free acid or base form.

The term addition salt as used hereinabove also comprises the solvates which the compounds of formula (I) as well as the salts thereof, are able to form. Such solvates are for example hydrates, alcoholates and the like.

The term stereochemically isomeric forms as used hereinbefore defines the possible different isomeric as well as conformational forms which the compounds of formula (I) may possess. Unless otherwise mentioned or indicated, the chemical designation of compounds denotes the mixture of all possible stereochemically and conformationally isomeric forms, said mixtures containing all diastereomers, enantiomers and/or conformers of the basic molecular structure. All stereochemically isomeric forms of the compounds of formula (I) both in pure form or in admixture with each other are intended to be embraced within the scope of the present invention.

Some compounds of the present invention may exist in different tautomeric forms and all such tautomeric forms are intended to be included within the scope of the present invention. For instance, compounds of formula (I) wherein Q is pyridinyl or quinolinyl substituted with hydroxy, may exist in their corresponding tautomeric form.

The N-oxide forms of the compounds of formula (I) are meant to comprise those compounds of formula (I) wherein one or several nitrogen atoms are oxidized to the so-called N-oxide, particularly those N-oxides wherein the piperidine-nitrogen is N-oxidized.

A first group of interesting compounds consists of those compounds of formula (I) wherein one or more of the following restrictions apply:
   a) —A—B— is a bivalent radical of formula (b-2), (b-3) or (b4); or
   b) Z is $Z^1$ wherein $Z^1$ is a bivalent radical of formula —CH$_2$—CH$_2$— or —CH$_2$—; or
   c) —A$^1$— is C$_{1-6}$alkanediyl, C$_{1-6}$alkanediyloxy, carbonyl, C$_{1-6}$alkanediyloxy substituted with hydroxy, or C$_{1-6}$alkanediyl substituted with hydroxy; in particular —A$^1$— is C$_{1-6}$alkanediyl; or
   d) —A$^2$— is a direct bond or C$_{1-6}$alkanediyl; in particular —A$^2$— is C$_{1-6}$alkanediyl;
   e) Q is phenyl, naphthalenyl, pyridinyl or quinolinyl, and optionally said Q is substituted with halo, C$_{1-6}$alkyl or C$_{1-6}$alkyloxy;
   f) R$^1$ is hydrogen, halo, formyl, C$_{1-4}$alkyl substituted with hydroxy, or a radical of formula (a-1) wherein X is a direct bond or C$_{1-4}$alkanediyl and R$^5$ is hydrogen, C$_{1-12}$alkyl, Ar or C$_{1-6}$alkyl substituted with Het;
   g) R$^2$ is hydrogen, halo, C$_{1-4}$alkyl, formyl, hydroxyC$_{1-4}$alkyl or C$_{1-4}$alkyloxycarbonyl;
   h) R$^3$ is hydrogen;
   i) R$^4$ is hydrogen, halo, C$_{1-6}$alkyl or C$_{1-6}$alkyloxy.

A second group of interesting compounds consists of those compounds of formula (I) wherein one or more of the following restrictions apply:
   a) —A—B— is a bivalent radical of formula (b-2), (b-3) or (b4); or
   b) Z is $Z^2$ wherein $Z^2$ is a bivalent radical of formula —C(=O)—CH$_2$—; or
   c) —A$^1$— is C$_{1-6}$alkanediyl, C$_{1-6}$alkanediyloxy, carbonyl, C$_{1-6}$alkanediyloxy substituted with hydroxyl or C$_{1-6}$alkanediyl substituted with hydroxy; in particular —A$^1$— is C$_{1-6}$alkanediyl; or
   d) —A$^2$— is a direct bond or C$_{1-6}$alkanediyl; in particular —A$^2$— is C$_{1-6}$alkanediyl;
   e) Q is phenyl, naphthalenyl, pyridinyl or quinolinyl, and optionally said Q is substituted with halo, C$_{1-6}$alkyl or C$_{1-6}$alkyloxy;
   f) R$^1$ is hydrogen, halo, formyl, C$_{1-4}$alkyl substituted with hydroxy, or a radical of formula (a-1) wherein X is a direct bond or C$_{1-4}$alkanediyl and R$^5$ is hydrogen, C$_{1-12}$alkyl, Ar or C$_{1-6}$alkyl substituted with Het;
   g) R$^2$ is hydrogen, halo, C$_{1-4}$alkyl, formyl, hydroxyC$_{1-4}$alkyl or C$_{1-4}$alkyloxycarbonyl;
   h) R$^3$ is hydrogen;
   i) R$^4$ is hydrogen, halo, C$_{1-6}$alkyl or C$_{1-6}$alkyloxy.

A particular group of compounds are those compounds of formula (I) wherein —A—B— is a bivalent radical of formula (b-2), (b-3) or (b4) wherein R$^8$ is hydrogen or halo; Z is —CH$_2$—CH$_2$—; —A$^1$— is —CH$_2$—CH$_2$—, —CH$_2$—CH$_2$—CH$_2$— or —O—CH$_2$—CH$_2$—; A$^2$— is —CH$_2$— and the dotted line is a bond.

Another particular group of compounds are those compounds of formula (I) wherein Q is 2-quinolinyl, 1-naphthalenyl, 2-naphthalenyl, phenyl or 2-pyridinyl and said Q is optionally substituted with C$_{1-4}$alkyl, halo, haloC$_{1-4}$alkyl or C$_{1-4}$alkyloxy.

A further particular group are those compounds of formula (I) wherein Q is 2-quinolinyl, 1-naphthalenyl, 2-naphthalenyl, 6-methyl-2quinolinyl, 6-chloro-2-pyridinyl, 4-methoxyphenyl, 3,5-dimethylphenyl, 3,5-difluorophenyl, or 3,5-bis(trifluoromethyl)phenyl.

Preferred compounds are those compounds of formula (I) wherein Z is —CH$_2$—CH$_2$—; —A—B— is —CH=CH—CH=CH—; —A$^1$— is —CH$_2$—CH$_2$— or —O—CH$_2$CH$_2$—; —A$^2$— is —CH$_2$—; R$^1$ is hydrogen, halo, formyl or a radical of formula (a-1) wherein X is a direct bond and R$^5$ is hydrogen, C$_{1-12}$alkyl, Ar or C$_{1-6}$alkyl substituted with Het; R$^2$ is hydrogen, C$_{1-4}$alkyl, formyl or C$_{1-4}$alkyloxycarbonyl; R$^3$ is hydrogen; R$^4$ is hydrogen or C$_{1-4}$alkyloxy and the dotted line is a bond.

Most preferred compounds of formula (I) are methyl 6,11-dihydro-11-[1-[2-[4-(2-quinolinylmethoxy)phenyl]ethyl]-4-piperidinylidene]-5H-imidazo[2,1-b][3]benzazepine-3-carboxylate;
dimethyl 6,11-dihydro-11-[1-[2-[4-(2-quinolinylmethoxy)phenyl]ethyl]-4-piperidinylidene]-5H-imidazo[2,1-b][3]benzazepine-2,3-dicarboxylate;
ethyl 6,11-dihydro-11-[1-[2-[4-(2-quinolinylmethoxy)phenyl]ethyl]-4-piperidinylidene]-5H-imidazo[2,1-b][3]benzazepine-3-carboxylate;
methyl 11-[1-[[3,5-dimethoxy-4-(2-quinolinylmethoxy)phenyl]methyl]-4-piperidinylidene]-6,11-dihydro-5H-imidazo[2,1-b][3]benzazepine-3-carboxylate;
methyl 6,11-dihydro-11-[1-[3-[4-(2-quinolinylmethoxy)phenyl]propyl]-4-piperidinylidene]-5H-imidazo[2,1-b][3]benzazepine-3-carboxylate;
methyl 6,11-dihydro-11-[1-[2-[4-(2-naphthalenylmethoxy)phenyl]ethyl]-4-piperidinylidene]-5H-imidazo[2,1-b][3]benzazepine-3-carboxylate;
methyl 6,11-dihydro-11-[1-[2-[4-(phenylmethoxy)phenyl]ethyl]-4-piperidinylidene]-5H-imidazo[2,1-b][3]benzazepine-3-carboxylate; and methyl 6,11-dihydro-11-[1-[2-[4-(1-naphthalenylmethoxy) phenyl]ethyl]-4-piperidinylidene]-5H-imidazo[2,1-b][3] benzazepine-3-carboxylate;

the stereoisomeric forms and the pharmaceutically acceptable addition salts thereof.

In the following paragraphs there are described different ways of preparing the compounds of formula (I). In order to simplify the structural formulae of the compounds of formula (I) and the intermediates intervening in their preparation, the fused imidazole moiety will be represented by the symbol T hereinafter.

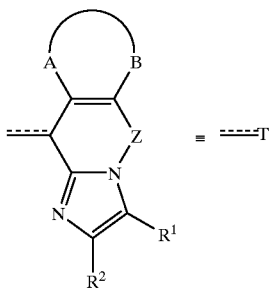

The compounds of the present invention can generally be prepared by N-alkylating an intermediate of formula (III) wherein W is an appropriate leaving group such as, for example, chloro, bromo, methanesulfonyloxy or benzenesulfonyloxy, with an intermediate of formula (II). The reaction can be performed in a reaction-inert solvent such as, for example, ethanol, dichloromethane, methyl isobutylketone or N,N-dimethylformamide, and in the presence of a suitable base such as, for example, sodium carbonate, sodium hydrogen carbonate or triethylamine. Stirring may enhance the rate of the reaction. The reaction may conveniently be carried out at a temperature ranging between room temperature and reflux temperature.

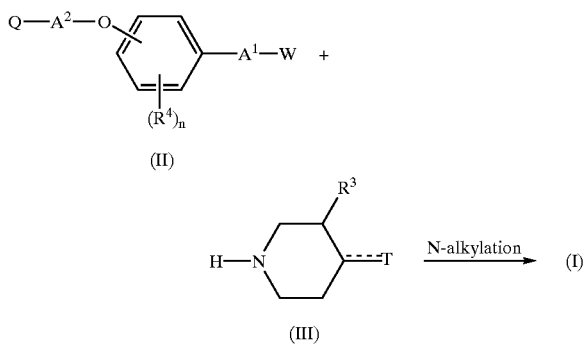

Compounds of formula (I) may also be prepared by O-alkylating an intermediate of formula (V) with an intermediate of formula (IV), wherein $W^1$ is an appropriate leaving group such as, for example, chloro, bromo, methanesulfonyloxy or benzenesulfonyloxy. The reaction can be performed in a reaction-inert solvent such as, for example, N,N-dimethylformamide, and in the presence of a suitable base such as, for example, sodium hydride, preferably at a temperature ranging between room temperature and reflux temperature.

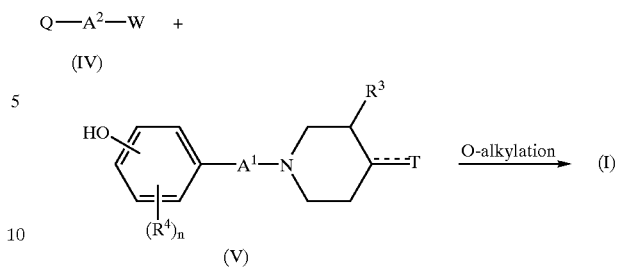

Compounds of formula (I) wherein —$A^{1'}$— represents $C_{1-6}$alkanediyl, $C_{1-6}$alkanediyloxy, $C_{1-6}$alkanediyloxyC$_{1-6}$alkanediyl, said compounds being represented by formula (I-i), may be prepared by reductive N-alkylation of an intermediate of formula (III) with an intermediate of formula (XIX). In said intermediate (XIX), —$A^{1''}$— represents a direct bond, $C_{1-5}$alkanediyl, $C_{1-5}$alkanediyloxy or a $C_{1-6}$alkanediyl-oxyC$_{1-5}$alkanediyl moiety whereby the formyl group is bonded on the $C_{1-5}$alkanediyl part.

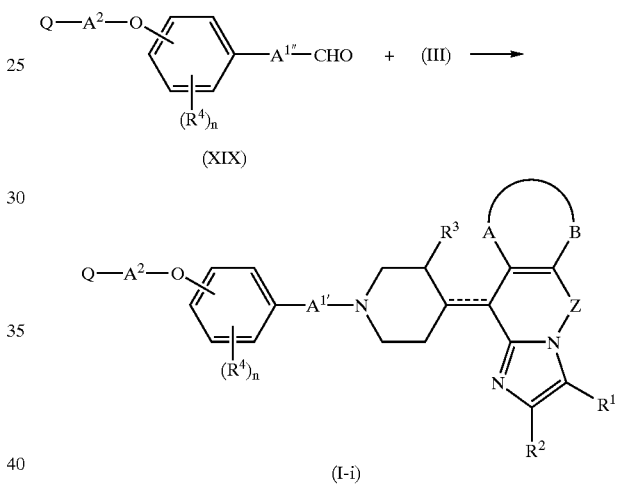

Said reductive N-alkylation may be performed in a reaction-inert solvent such as, for example, dichloromethane, ethanol, toluene or a mixture thereof, and in the presence of a reducing agent such as, e.g. sodium borohydride, sodium cyanoborohydride or triacetoxy borohydride. It may also be convenient to use hydrogen as a reducing agent in combination with a suitable catalyst such as, for example, palladium-on-charcoal or platinum-on-charcoal. In case hydrogen is used as reducing agent, it may be advantageous to add a dehydrating agent to the reaction mixture such as, for example, aluminium tert-butoxide. In order to prevent the undesired further hydrogenation of certain functional groups in the reactants and the reaction products, it may also be advantageous to add an appropriate catalyst-poison to the reaction mixture, e.g., thiophene or quinoline-sulphur. To enhance the rate of the reaction, the temperature may be elevated in a range between room temperature and the reflux temperature of the reaction mixture.

In the following paragraphs there are described different ways of converting compounds of formula (I) into each other following art-known functional group transformation procedures. In order to simplify the structural formulae of the compounds of formula (I), the substituted piperidine moiety will be represented by the symbol M hereinafter.

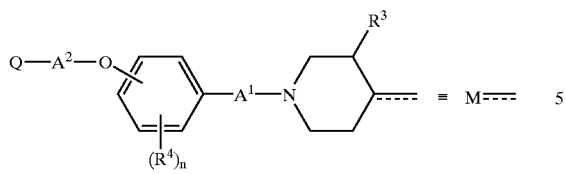

For instance, compounds of formula (I) wherein $R^1$ is $C_{1-4}$alkyl substituted with hydroxy, said compounds being represented by formula (I-a), may be converted in the corresponding compounds of formula (I) wherein $R^1$ is $C_{1-4}$alkylcarbonyloxy$C_{1-4}$alkyl, said compounds being represented by formula (I-b), according to art-known esterification methods such as, e.g. treatment with an acyl halide in the presence of a base to pick up the acid liberated during the reaction.

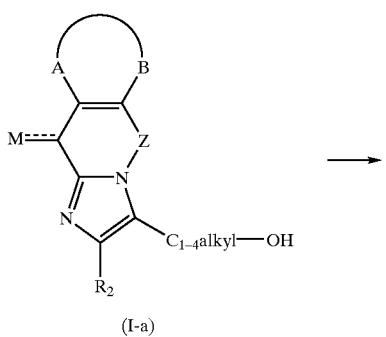

(I-a)

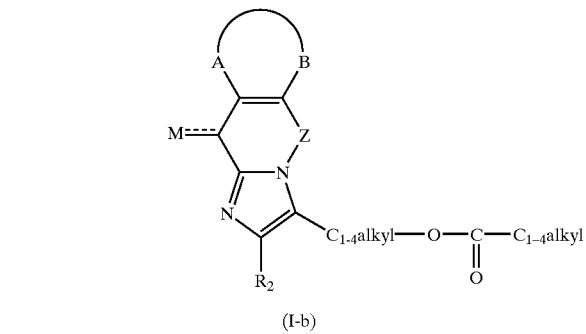

(I-b)

Also, compounds of formula (I-a) wherein $R^1$ is $CH_2OH$, said compounds being represented by formula (I-a-1), may be converted in the corresponding compounds of formula (I) wherein $R^1$ is CHO, said compounds being represented by formula (I-c), by oxidation with a suitable reagent such as, e.g. manganese(IV)oxide.

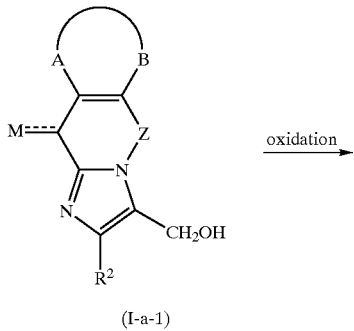

(I-a-1)

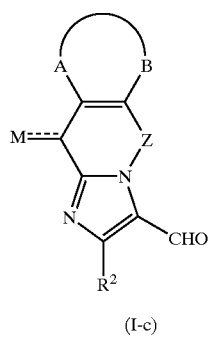

(I-c)

Further, compounds of formula (I) wherein $R^1$ contains a carboxyl group, said compounds being represented by formula (I-d), may be converted in the corresponding esters by art-known methods such as, e.g. treatment with an alcohol in the presence of an acid or base.

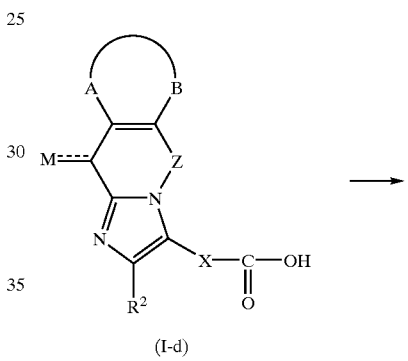

(I-d)

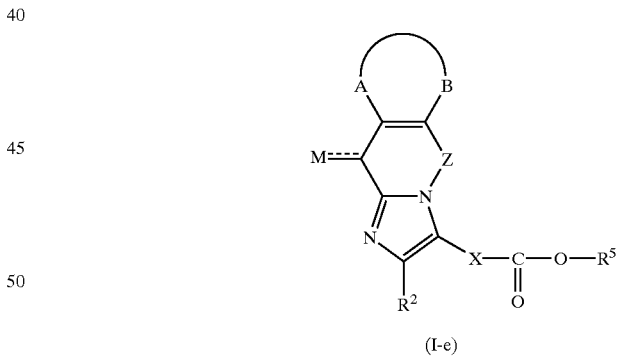

(I-e)

Conversely, compounds of formula (I-e) may be hydrolyzed into compounds of formula (I-d), in the presence of an acid or a base.

The compounds of formula (I-c) may be converted into compounds of formula (I) wherein $R^1$ is a methoxycarbonylmethyl, said compounds being represented by formula (I-f), by treatment with methyl methylthiomethyl sulfoxide in the presence of benzyltrimethyl ammonium hydroxide in a reaction-inert solvent, e.g. tetrahydrofuran.

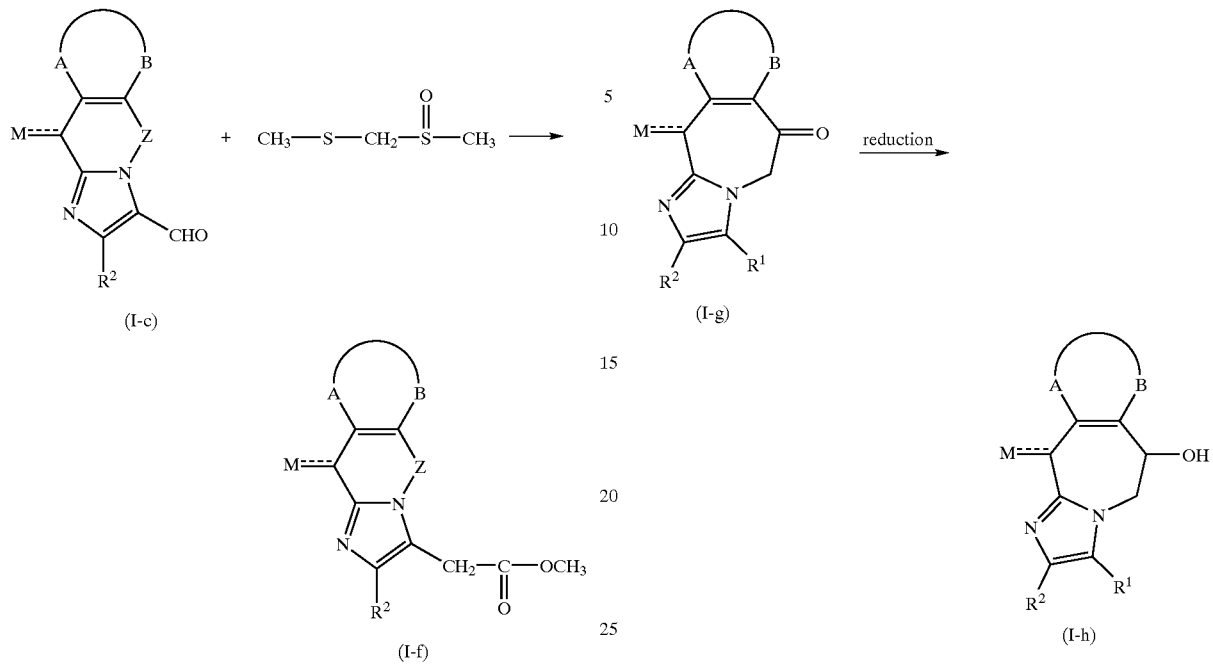

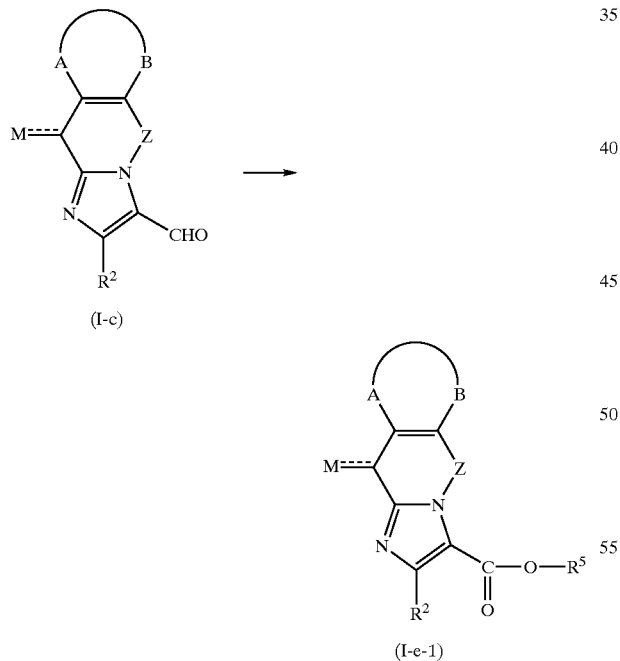

Also, compounds of formula (I-c) may be converted into compounds of formula (I-e) wherein X is a direct bond, said compounds being represented by formula (I-e-1), by treatment with an; alcohol, such as, e.g. methanol or ethanol, in the presence of acetic acid, $MnO_2$ and NaCN.

Compounds of formula (I) wherein $Z^2$ represents —C(=O)—$CH_2$—, said compounds being represented by formula (I-g), can be converted in the corresponding alcohols by art-known reduction procedures such as, e.g. treatment with sodiumborohydride in a suitable solvent, e.g. methanol.

The starting materials and some of the intermediates are known compounds and are commercially available or may be prepared according to conventional reaction procedures generally known in the art. For example, a number of intermediates of formula (III), especially those wherein Z is $Z^2$, are known compounds which may be prepared according to art-known methodologies described in EP-0,518,435-A, EP-0,518,434-A and WO-95/02600.

In the following paragraphs there are described several methods of preparing the intermediates employed in the foregoing preparations.

The intermediates of formula (II) may be prepared by O-alkylating the aromatic hydroxyl group of intermediate (VI) with an intermediate of formula (IV), wherein $W^1$ is a suitable leaving group such as, e.g. halo, methanesulfonyloxy or benzenesulfonyl-oxy, and subsequent conversion of the hydroxy group of intermediate (VII) into leaving group W, e.g. by treating intermediate (VII) with methanesulfonyloxy chloride or a halogenating reagent such as, e.g. $POCl_3$.

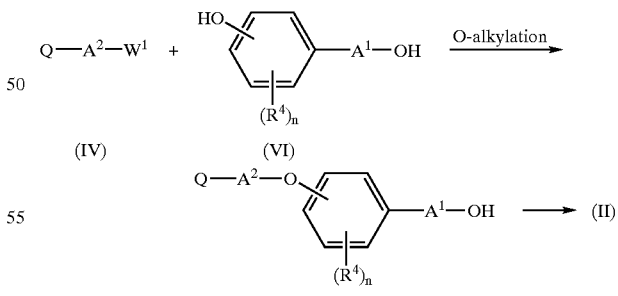

Said O-alkylation reaction can conveniently be carried out by mixing the reactants in a reaction-inert solvent such as, for example, methanol or N,N-dimethylformamide, and in the presence of an appropriate base such as, e.g. sodium carbonate or sodium hydrogen carbonate, preferably at a temperature ranging between room temperature and the reflux temperature of the reaction mixture.

Also, intermediates of formula (II) wherein —A¹— is C$_{1-6}$alkanediyloxy, said intermediates being represented by compounds of formula (II-a), may be prepared by reacting an intermediate of formula (VIII) with an intermediate of formula (IX) in the presence of an appropriate base such as, e.g. potassium carbonate, and optionally in the presence of a reaction-inert solvent such as, for example, N,N-dimethylformamide, acetonitrile or tetrahydrofuran. Subsequent conversion of the hydroxy group into a leaving group W, e.g. by treatment with methanesulfonyloxy chloride or a halogenating reagent such as, e.g. POCl$_3$, yields intermediates of formula (II-a). It may be advantageous to conduct said O-alkylation reaction at a temperature ranging between

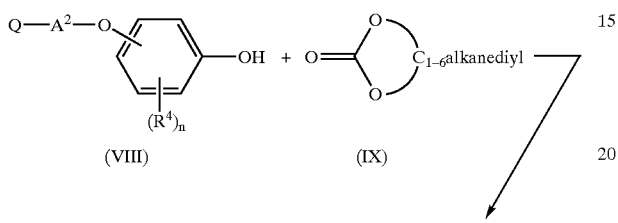

(VIII)    (IX)

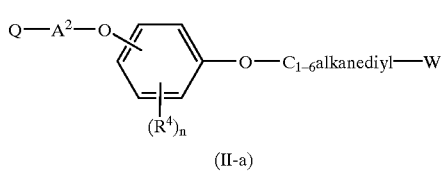

(II-a)

In an embodiment, the present invention also provides for novel compounds of formula (II), represented by compounds of formula (II-b) wherein radical —A¹'— represents C$_{1-6}$alkanediyl, C$_{1-6}$alkanediyloxy or C$_{1-6}$alkanediyloxyC$_{1-6}$alkanediyl and Q¹ represents all substituents Q other than unsubstituted phenyl.

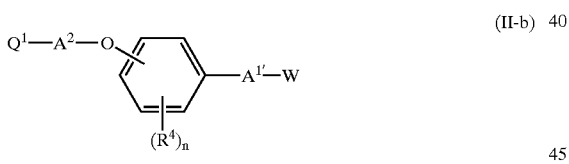

(II-b)

Intermediates of formula (V) wherein —A¹'— represents C$_{1-6}$alkanediyl, C$_{1-6}$alkanediyloxy, C$_{1-6}$alkanediyloxyC$_{1-6}$alkanediyl, said intermediates being represented by formula (V-a), may be prepared by reductive N-alkylation of an intermediate of formula (III) with an intermediate of formula (X). Optionally, intermediate (X) has a protected hydroxyl group which can be deprotected using art-known methods subsequent to the reductive N-alkylation. In said intermediate (X), —A¹''— represents a direct bond, C$_{1-5}$alkanediyl, C$_{1-5}$alkanediyloxy or C$_{1-6}$alkanediyl-oxyC$_{1-5}$alkanediyl whereby the formyl group is bonded on the C$_{1-5}$alkanediyl part. Said reductive N alkylation may be performed according to the hereinabove described procedure.

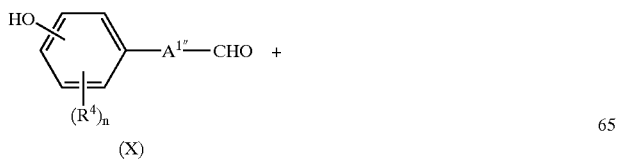

(X)

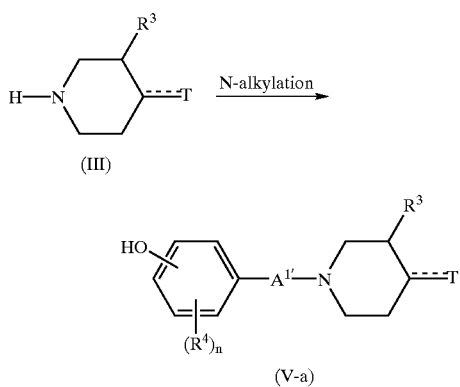

(III)

(V-a)

Intermediates of formula (III-a), defined as intermediates of formula (III) wherein Z is Z¹, may be prepared according to scheme I.

Scheme I

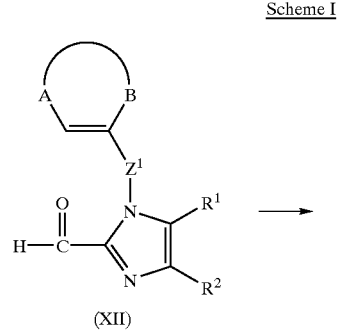

(XII)

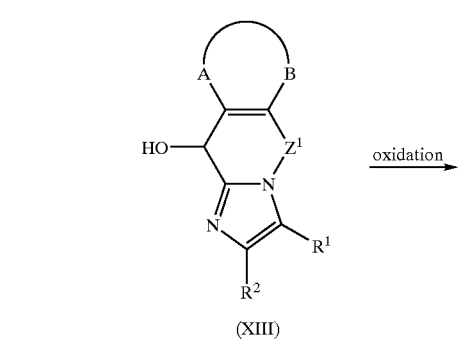

(XIII)

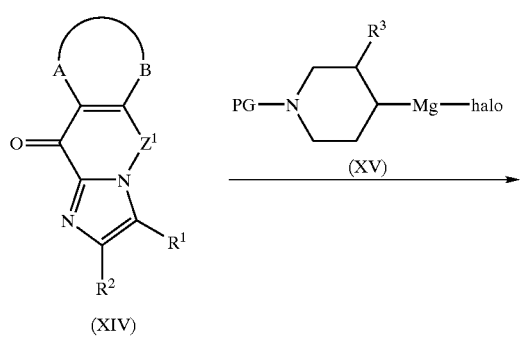

(XIV)    (XV)

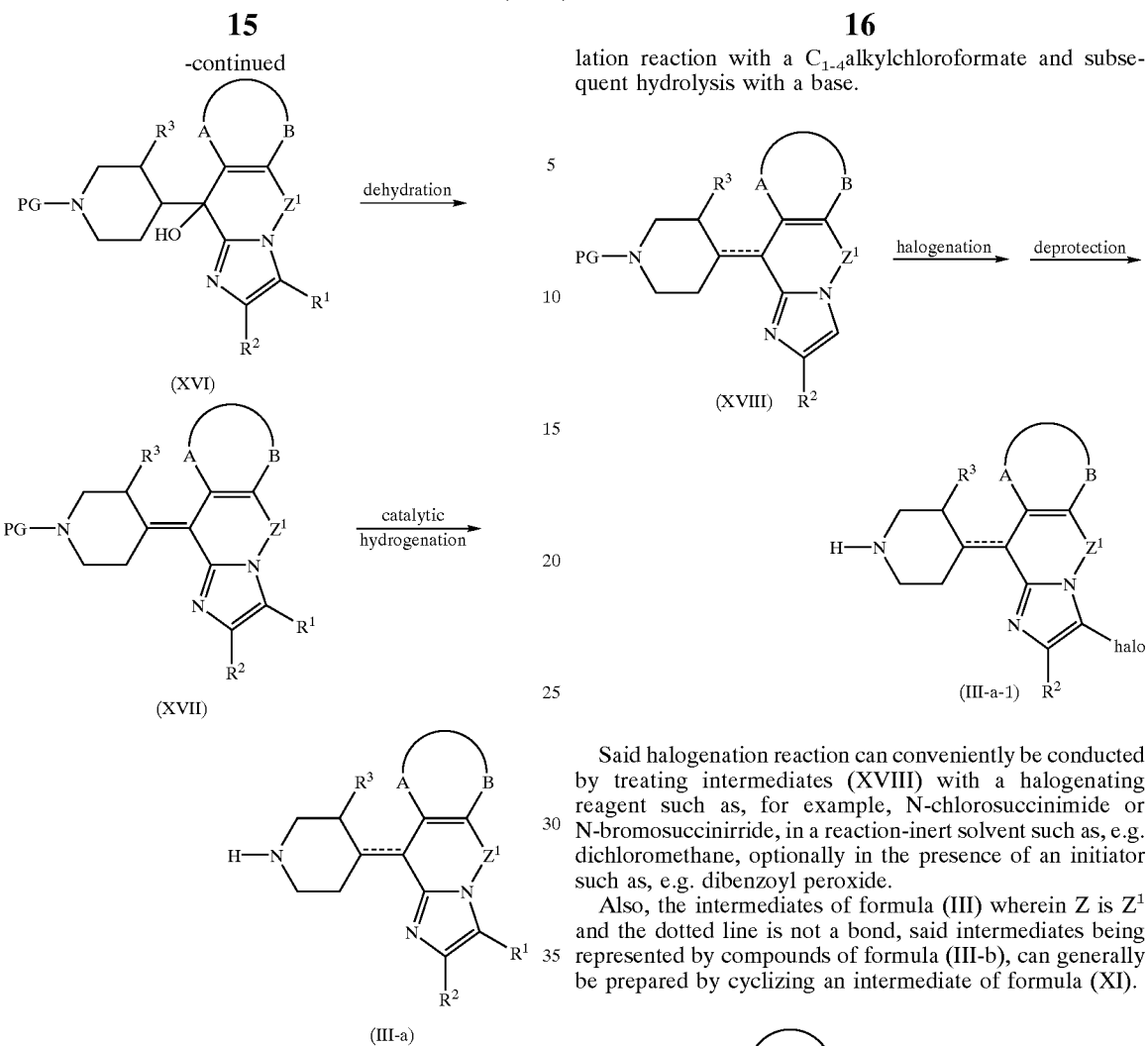

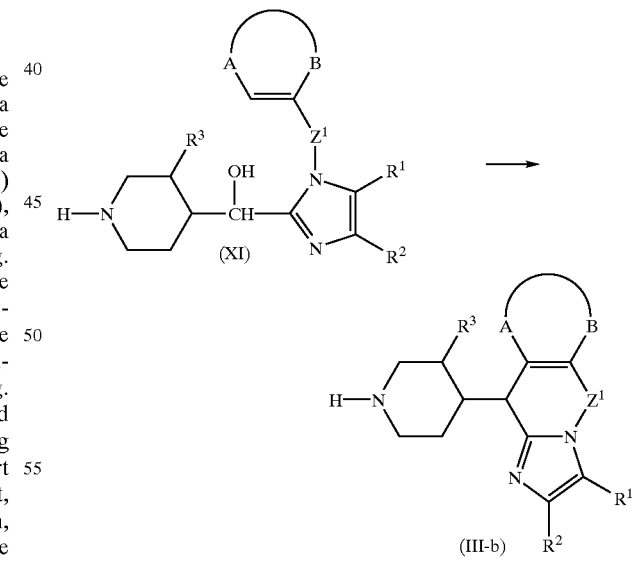

In scheme I, an intermediate of formula (XII) can be cyclized in an analogous way as an intermediate of formula (XI), giving an alcohol of formula (XIII) which can be oxidized following art-known oxidation methods into a ketone of formula (XIV). An intermediate of formula (XVI) can be prepared by addition of a Grignard reagent (XV), wherein PG is a suitable protecting group, e.g. benzyl, to a ketone of formula (XIV) in a reaction-inert solvent, e.g. tetrahydrofuran. An intermediate of formula (III-a) can be prepared by dehydration of an intermediate (XVI) subsequently with catalytic hydrogenation of an intermediate (XVII). Said dehydration reaction can conveniently be conducted employing conventional dehydrating reagents, e.g. sulfuric acid, following art-known methodologies. Said catalytic hydrogenation reaction can be conducted following art-known procedures, e.g. stirring in a reaction-inert solvent, e.g. methanol, in the presence of a suitable catalyst, e.g. palladium-on-carbon and in the presence of hydrogen, optionally the temperature may be elevated in a range between room temperature and the reflux temperature of the reaction mixture and, if desired, the pressure of the hydrogen gas may be raised.

Further, intermediates of formula (III-a) wherein $R^1$ is halo, said intermediates being represented by formula (III-a-1), can be prepared by halogenating intermediates of formula (XVIII) wherein PG is a protective group such as, e.g. $C_{1-6}$alkyl, and subsequent depiotection. For instance, when PG is $C_{1-6}$alkyl, PG may be removed by a carbonylation reaction with a $C_{1-4}$alkylchloroformate and subsequent hydrolysis with a base.

Said halogenation reaction can conveniently be conducted by treating intermediates (XVIII) with a halogenating reagent such as, for example, N-chlorosuccinimide or N-bromosuccinirride, in a reaction-inert solvent such as, e.g. dichloromethane, optionally in the presence of an initiator such as, e.g. dibenzoyl peroxide.

Also, the intermediates of formula (III) wherein Z is $Z^1$ and the dotted line is not a bond, said intermediates being represented by compounds of formula (III-b), can generally be prepared by cyclizing an intermediate of formula (XI).

Said cyclization reaction is conveniently conducted by treating an intermediate of formula (XI) with an appropriate acid, yielding an intermediate of formula (III-a). Appropriate acids are, for example, methanesulfonic acid or trifluoromethanesulfonic acid. It should be noted that only those intermediates of formula (III-a) wherein $R^1$ and $R^2$ are stable under the given reaction conditions can be prepared according to the above reaction procedure.

Compounds of formula (I) and some of the intermediates may have one or more stereogenic centers in their structure, present in a R or a S configuration.

The compounds of formula (I) as prepared in the hereinabove described processes may be synthesized as a mixture of stereoisomeric forms, in particular in the form of racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I), the N-oxide forms, the pharmaceutically acceptable addition salts and stereoisomeric forms thereof have valuable pharmacological properties in that they inhibit transport of a chemotherapeutic agent through a membrane by a inembrane-associated transporter, especially the membrane-associated transporter P-glycoprotein, and thereby inhibit or reverse the effects of multidrug resistance, as can be evidenced by the results obtained in the MDR in vitro test (Example C-1) and the MDR in vivo test (Example C-2).

In view of their MDR inhibiting properties, the compounds of formula (I) are usable for the manufacture of a medicine to improve the oral bioavailability of pharmaceutical agents that are poorly absorbed or not absorbed at all from the gastrointestinal tract or gut by pre-administering and/or simultaneously administering to a warm-blooded animal by the oral route a compound of formula (I). As demonstrated in Example C-3 the compounds of formula (I) are able to improve oral bioavailability.

The improved oral bioavailability of a second pharmaceutical agent when co-administered with a compound of formula (I) can be determined by measuring the total systemic concentration of said pharmaceutical agent over time after co-administration of said pharmaceutical agent and a compound of formula (I) and after administration of only the pharmaceutical agent. The increase in drug bioavailability is defined as an increase in the Area Under the Curve (AUC). AUC is the integrated measure of systemic drug concentrations over time in units of mass-time/volume. The AUC from time zero (the time of dosing) to time infinity (when no drug remains in the body) following the administration of a drug dose is a measure of the exposure of the test subject, i.e. an animal or a human patient, to the drug.

Co-administration of a compound of formula (I) and a second pharmaceutical agent that is poorly absorbed or not absorbed at all from the gastrointestinal tract comprehends administration substantially simultaneously with said pharmaceutical agent (either less than 30 minutes before, less than 30 minutes after or together), from about 30 minutes to about 24 hours before the administration of the pharmaceutical agent, or both, i.e. with one or more doses of the same compound of formula (I) given at least 30 minutes before and one dose given simultaneously with (either together with or immediately before or after) the pharmaceutical agent. In general, "co-administration" means the first pharmaceutical compound of formula (I) and the second pharmaceutical agent are present in the gut lumen and/or membranes during at least partially overlapping times. Additionally, "co-administration" comprehends administering more than one dose of said pharmaceutical agent within 24 hours after a dose of the compound of formula (I), in other words, the compound of formula (I) need not be administered again before or with every administration of said pharmaceutical agent, but may be administered intermittently during the course of treatment.

Suitable pharmaceutical agents for use in the combinations defined above include are, e.g., anti-neoplastic agents such as, e.g. paclitaxel (Taxol®), docetaxel (Taxotere®), other related taxanes, adriamycine, cladribine, cisplatin, cyclophosphamide, dactinomycin, daunorubicin, doxorubicin, etoposide, finasteride, 5-fluorouracil, irinotecan, leucovorin, mitomycin, mitoxantrone, tamoxifen, topotecan, trimetrexate, vincristine, vinblastine and the like.

Other suitable pharmaceutical agents can be compounds from classes, such as, but not limited to, aminoacridines, aminoquinolines, anilides, anthracycline antibiotics, antiestrogens, benzofurans, benzhydryl compounds, benzazepines, cannabioids, cephalosporines, colchicine, cyclic peptides, dibenzazepines, epipodophyllotoxins, flavonoids, flavones, imidazoles, isoquinolines, macrolides, opioids, phenylakylamines, phenothiazines, piperazines, piperidines, pyrrololidines, quinazolines, quinolines, quinones, rauwolfia alkaloids, retinoids, salicylates, sorbitans, steroids, triazoles, unsaturated fatty acids and vinca alkaloids.

Diseases, disorders or conditions wherein the above-mentioned anti-neoplastic agents are used are, for example, neoplastic diseases caused by the growth of neoplasms (or tumors) such as, for example, haematological tumors (leukemias, lymphomas), renal carcinoma, melanoma, ovarian cancer, breast cancer, lung cancer, head and neck carcinomas, hepatocellular carcinoma, liver metastases, genito-urinary and gastrointestinal tract cancers and Kaposi's sarcoma.

The first pharmaceutical compound of formula (I) is used in combination with a second pharmaceutical agent that is poorly absorbed or not absorbed at all from the gastrointestinal tract. The invention thus provides a combination containing a composition as defined herein comprising a first pharmaceutical compound of formula (I), together with a composition as defined herein comprising a second pharmaceutical agent, in particular an anti-neoplastic agent. The combination may be orally administered separately, simultaneously or consecutively, or the combination may also be presented in the form of one pharmaceutical formulation. Thus, a pharmaceutical product comprising (a) a first pharmaceutical compound of formula (I) and (b) a second pharmaceutical agent that is poorly absorbed or not absorbed at all from the gastrointestinal tract, as a combined preparation for simultaneous, separate or sequential use in the therapeutic or prophylactic treatment of warm-blooded animals. Such a product may comprise a kit comprising a container containing a pharmaceutical composition of a compound of formula (I), and another container comprising a pharmaceutical composition of the pharmaceutical agent that is poorly absorbed or not absorbed at all from the gastrointestinal tract. The product with separate compositions of the two active ingredients has the advantage that appropriate amounts of each component, and timing and sequence of administration can be selected in function of the patient.

When compounds of formula (I) are used in combination with a second pharmaceutical agent that is poorly absorbed or not absorbed at all from the gastrointestinal tract, the dose of said pharmaceutical agent may vary from the dose when used alone.

For oral administration, when compounds of formula (I) are co-administered with a second pharmaceutical agent the dose of the latter may be the same or more commonly, lower, than the dose employed when the pharmaceutical agent is used alone. Appropriate doses will be readily appreciated by those skilled in the art.

Pharmaceutical agents that are so poorly absorbed from the gastrointestinal tract that no oral dosage form is available may become suitable for oral administration when used in combination with a compound of formula (I).

In view of the above uses of the compounds of formula (I), it follows that the present invention also provides a method of improving the bioavailability upon oral co-administration to a warm-blooded animal, in particular to a human, of a second pharmaceutical agent. Said method comprises the oral co-administration to said warm-blooded animal of a second pharmaceutical agent that is poorly or not absorbed at all from the gastrointestinal tract and a compound of formula (I). Also provided is a method wherein the compound of formula (I) and the pharmaceutical agent are each administered in a separate oral dosage form or in a combination oral dosage form.

For ease of administration, the subject compounds may be formulated into various pharmaceutical forms for administration purporses. To prepare the pharmaceutical compositions of this invention, an effective amount of the particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. Acid addition salts of (I) due to their increased water solubility over the corresponding base form, are obviously more; suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The compositions may advantageously be presented in discrete dose units, especially in unit dosage forms. A convenient unit dose formulation contains the active ingredient in an amount of from 0.1 to 1000 mg, and in particular from 1 to 200 mg. The amount of a compound of formula (I) required as daily dose in treatment will vary not only with the particular compound selected, but also with the route of administration, the nature of the condition being treated and the age, weight and condition of the patient and will ultimately be at the discretion of the attendant physician. In general, however, a suitable daily dose will be in the range of from about 0.1 to about 5000 mg per day, in particular from about 1 to 1000 mg per day, more particular from about 10 to 500 mg per day. Other daily dosing schemes are administration of twice-daily doses of 200 or 300 mg. A suitable daily dose for use in prophylaxis will generally be in the same range.

The following examples are provided for purposes of illustration, not limitation.

Experimental Part

A. Preparation of the Intermediates

Hereinafter "THF" means tetrahydrofuran, "DIPE" means diisopropylether, "DCM" means dichloromethane, "DMF" means N,N-dimethylformamide and "ACN" means acetonitrile.

EXAMPLE A.1 a) 4-Hydroxybenzeneethanol (103.5 g) was stirred in ethanol (1.5 l), at room temperature. A solution of potassium hydroxide (84 g) in ethanol (1.5 l) was added dropwise, over a 1 hour period. 2-(Chloromethyl)quinoline monohydrochloride was added portionwise over a 25-minutes period. The reaction mixture was stirred and refluxed for 12 hours. The reaction mixture was poured out into water (5 l) and this mixture was stirred vigorously. The precipitate was filtered off, and washed with water (2 l). Toluene was added and azeotroped on the rotary evaporator. The residue was dried, yielding 187 g (89%) of 4-(2-quinolinylmethoxy)benzeneethanol (intermediate 1, mp. 144.8° C.).

b) A mixture of intermediate 1 (2.79 g) and N,N-diethylethanamine (1.2 g) in DCM (50 ml) was stirred on an ice bath. Methanesulfonyl chloride (1.26 g) was added drop-wise at a temperature below 10° C. The mixture was brought to room temperature and then stirred for 1 hour. Water was added and the mixture was extracted with DCM. The organic layer was washed with water, dried, filtered and evaporated, yielding 3.8 g (100%) of 4-(2-quinolinylmethoxy)benzeneethanol methanesulfonate(ester)(interm. 2). In a similar way, 3-(2-quinolinylmethoxy)benzeneethanol methanesulfonate(ester) (intermediate 3) and 4-[(6-methyl-2-quinolinyl)methoxy]benzeneethanol methanesulfonate (ester) (intermediate 4) were synthesized.

EXAMPLE A.2 a) 3-(2-Quinoliniyl-methoxy)phenol (12.5 g), potassium carbonate (10.4 g) and 1,3-dioxolan-2-one (44 g) were stirred on an oil bath at 100° C. for 2 hours. The mixture was cooled, poured into water and extracted with DCM. The organic layer was dried, filtered and evaporated. The residue was purified by column chromatography over silica gel (eluent: CH$_2$Cl$_2$/CH$_3$OH 97/3). The pure fractions were collected and evaporated. The residue was stirred up in DIPE. The precipitate was filtered off and dried, yielding 11.9 g (80.6%) of 2-[3-(2-quinolinyl-methoxy)phenoxy]ethanol (intermediate 5).

b) A mixture of intermediate 5 (2.95 g) and N,N-diethylethanamine (1.2 g) in DCM (50 ml) was stirred on an ice bath. Methanesulfonyl chloride (1.26 g) was added dropwise at a temperature below 5° C. The mixture was brought to room temperature and then stirred for 1 hour. Water was added and the mixture was stirred. The mixture was separated and the aqueous layer was extracted with DCM. The combined organic layers were washed with water, dried, filtered and evaporated, yielding 4.5 g (100%) of 2-[3-(2-quinolinyl-methoxy)phenoxy]ethanol methanesulfonate(ester) (intermediate 6). In a similar way, 2-[4-(2-quinolinylmethoxy)phenoxy]ethanol methanesulfonate(ester) (intermediate 7) was synthesized.

EXAMPLE A.3

A mixture of 3,5-dimethoxy-4-hydroxybenzaldehyde (8 g) and 6,11-dihydro-11-(4-piperidinylidene)-5H-imidazo[2,1-b][3]benzazepine (9 g) in methanol (250 ml) and thiophene (4%, 3 ml) was hydrogenated at room temperature with palladium on activated carbon (10%, 2 g) as a catalyst. After uptake of hydrogen (1 equivalent), the catalyst was filtered off and the filtrate was evaporated. The residue was purified by column chromatography over silica gel (eluent: CH$_2$Cl$_2$/CH$_3$OH 95/5). The pure fractions were collected and evaporated, yielding 9.5 g (65%) of 4-[4-(5,6-dihydro-11H-imidazo[2,1-b][3]benzazepin-11-ylidene)-1-piperidinyl]-2,6-dimethoxyphenol (intermediate 8).

In a similar way, 6,11-dihydro-11-[1-[(4-hydroxy-3,5-dimethoxyphenyl)methyl]-4-piperidinylidene]-5H-imidazo[2,1-b][3]benzazepine-3-methanol (intermediate 9) was synthesized.

EXAMPLE A.4

A mixture of α-[1-(phenylmethyl)-1H-imidazol-2-yl]-4-piperidinemethanol (5.4 g) in trifluoromethanesulfonic acid (25 ml) was stirred overnight at 100° C. The reaction mixture was cooled, poured out onto ice, then alkalized with NaOH and this mixture was extracted with DCM. The separated organic layer was dried, filtered and the solvent was evaporated. The residue was purified over silica gel on a glass filter (eluent :CH$_2$Cl$_2$/(CH$_3$OH/NH$_3$) 95/5, upgrading to 90/10). The pure fractions were collected and the solvent was evaporated, yielding 2.5 g (50%) of 5,10-dihydro-10-(4-piperidinyl)-imidazo[1,2-b]isoquinoline (intermediate 10).

EXAMPLE A.5 a) 6,11-Dihydro-11-(1-methyl-4-piperidinylidene)-5H-imidazo[2,1-b][3]benzazepine (28 g) was stirred in DCM (500 ml), until complete dissolution. Dibenzoyl peroxide (0.1 g) was added. N-chlorosuccinimide (13.4 g) was added portionwise and the resulting reaction mixture was stirred overnight at room temperature, then for 2 hours at reflux temperature. The solvent was evaporated. The residue was purified by column chromatography over silica gel (eluent: CH$_2$Cl$_2$/(CH$_3$OH/NH$_3$) 97/3, upgrading to 95/5). The pure fractions were collected and the solvent was evaporated. The residue was crystallized from ACN. The precipitate was filtered off and dried, yielding 23.3 g (74%) of 3-chloro-6,11-dihydro-11-(1-methyl-4-piperidinylidene)-5H-imidazo-[2,1-b][3]benzazepine (intemediate 11).

b) A mixture of intermediate 11 (31.4 g) and N,N-diethylethanamine (20.2 g) in toluene (1 l) was stirred and refluxed. Ethyl chloroformate (65.1 g) was added dropwise. The reaction mixture was stirred and refluxed for 90 minutes. The mixture was cooled. Water and K$_2$CO$_3$ were added and the layers were separated. The aqueous layer was extracted with toluene. The organic layer was separated, dried (MgSO$_4$), filtered and the solvent was evaporated. The residue was crystallized from DIPE. The precipitate was filtered off and dried, yielding 32.4 g (87%) of ethyl 4-(3-chloro-5,6-dihydro-11H-imidazo[2,1-b][3]benzazepin-11-ylidene)-1-piperidinecarboxylate (intermediate 12).

c) A mixture of intermediate 12 (30.4 g) and potassium hydroxide (46 g) in isopropanol (370 ml) was stirred and refluxed for 6 hours. The solvent was evaporated. The residue was taken up in water and extracted with DCM. The organic layer was separated, dried (MgSO$_4$), filtered and the solvent was evaporated. The residue was crystallized from ACN. The precipitate was filtered off and dried, yielding 1.65 g (90%) of 3-chloro-6,11-dihydro-11-(4-piperidinylidene)-5H-imidazo[2,1-b][3]benzazepine (intermediate 13).

B. Preparation of the Final Products

EXAMPLE B.1

A mixture of intermediate 2 (8.6 g), intermediate 13 (6 g) and sodium hydrogen carbonate (2.2 g) in ethanol (300ml) was stirred and refluxed for 48 hours. The solvent was evaporated and the residue was taken up in water and DCM. The layers were separated and the aqueous layer was extracted with DCM. The organic layer was separated, dried (MgSO$_4$), filtered and the solvent was evaporated. The residue was purified on a glass filter over silica gel (eluent: CH$_2$Cl$_2$/(CH$_3$OH/NH$_3$) 95/5). The pure fractions were collected and the solvent was evaporated. The residue was crystallized from ethanol. The precipitate was filtered off and dried, yielding 8.21 g (73%) of 3-chloro-6,11-dihydro-11-[1-[2-[4-(2-quinolinylmethoxy)phenyl]ethyl]-4-piperidinylidene]-5H-imidazo[2,1-b][3]benzazepine (compound 13). In a similar way, 6,11-dihydro-11-[1-[2-[4-(2-quinolinylmethoxy)phenyl]ethyl]-4-piperidinylidene]-5H-imidazo[2,1-b][3]benzazepine-3-methanol (compound 2) was synthesized.

EXAMPLE B.2

2-(Chloromethyl)quinoline monohydrochloride (4.06 g) was taken up in water, alkalized with K$_2$CO$_3$ and extracted with DCM. The organic layer was dried (MgSO$_4$), filtered and evaporated, yielding 2-(chloromethyl)quinoline. Sodium hydride (0.7 g) was added at room temperature to a solution of intermediate 8 (6.5 g) in DMF (350 ml) and the mixture was stirred for 30 minutes. 2-(Chloromethyl)

quinoline dissolved in DMF was added and the mixture was stirred at 50° C. for 3 hours. The mixture was evaporated, the residue was taken up in water and extracted with DCM. The organic layer was dried(MgSO$_4$), filtered and evaporated. The residue was crystallized from ACN, the precipitate was filtered off, yielding 5.52 g (64%) of 11-[1-[[3,5-dimethoxy-4-(2-quinolinylmethoxy)-phenyl]methyl]-4-piperidinyl-idene]-6,11-dihydro-5H-imidazo[2,1-b][3]benzazepine (compound 32, mp. 214.8° C.).

EXAMPLE B.3

A mixture of compound 2 (5.56 g) and N,N-diethylethanamine (1.2 g) in DCM (100 ml) was stirred at room temperature till complete dissolution. A solution of acetyl chloride (0.86 g) in DCM was added dropwise. The mixture was stirred at room temperature for 1 hour. K$_2$CO$_3$ (2 g) and water were added and the mixture was separated into its layers. The aqueous layer was extracted with DCM. The combined organic layer was dried (MgSO$_4$), filtered and the solvent was evaporated. The residue was crystallized from ACN. The precipitate was filtered off and dried, yielding 3.95 g (66%) of [5,6-dihydro-11-[1-[2-[4-(2-quinolinylmethoxy)phenyl]ethyl]-4-piperidinylidene]-11H-imidazo[2,1-b][3]benzazepine-3-yl]methanol acetate(ester) (compound 3).

EXAMPLE B.4

Compound 2 (206 g) was dissolved in DCM (11 l) under continuous stirring. Manganese dioxide (450 g) was added in 100-g portions and the resulting reaction mixture was stirred for 1 hour. The mixture was filtered over dicalite and the filtrate was evaporated. The residue was stirred in ACN, filtered off and dried, yielding 170 g (83%) of 6,11-dihydro-11-[1-[2-[4-(2-quinolinylmethoxy)phenyl]ethyl]-4-piperidinylidene]-5H-imidazo[2,1-b][3]benzazepine-3-carboxaldehyde (compound 4, mp. 193.5° C.).

EXAMPLE B.5

A mixture of compound 4 (8.32 g) and methyl methylthiomethyl sulfoxide (MMTS) (4.5 g) in THF (100 ml) and benzyltrimethyl ammonium hydroxide (40% in methanol; 20 ml) was stirred and refluxed overnight. The solvent was evaporated. The residue was taken up in water and extracted with DCM. The organic layer was separated, dried (MgSO$_4$), filtered and the solvent was evaporated. Toluene was added twice and evaporated again. The residue was taken up in methanol (50 ml). HCl gas was bubbled through the mixture, cooled on an ice bath, for 30 minutes. The mixture was stirred overnight. The solvent was evaporated. The residue was taken up in water, alkalized with K$_2$CO$_3$ and extracted with DCM. The organic layer was separated, dried, filtered and the solvent was evaporated. The residue was purified over silica gel on a glass filter (eluent: CH$_2$Cl$_2$/CH$_3$OH 95/5). The pure fractions were collected and the solvent was evaporated. The residue was crystallized from ACN. The precipitate was filtered off and dried, yielding 2.7 g (30%) of methyl 6,11-dihydro-11-[1-[2-[4-(2-quinolinylmethoxy)phenyl]ethyl]-4-piperidinylidene]-5H-imidazo[2,1-b][3]-benzazepine-3-acetate (compound 5).

EXAMPLE B.6

A mixture of compound 4 (164 g), sodium cyanate (80 g) and manganese dioxide (500 g) in methanol (5.5 l) was stirred at room temperature. Ethanoic acid (122 g) was added dropwise and the resulting reaction mixture was stirred and refluxed overnight. The reaction mixture was filtered over dicalite, and the filter residue was rinsed with CH$_3$OH/CH$_2$Cl$_2$. The filtrate was evaporated. The residue was partitioned between DCM and aqueous K$_2$CO$_3$ solution. The organic layer was separated, dried (MgSO$_4$), filtered and the solvent was evaporated. The residue was crystallized from ACN. The precipitate was filtered off and dried, yielding 152 g (87%) of methyl 6,11-dihydro-11-[1-[2-[4-(2-quinolinylmethoxy)phenyl]ethyl]-4-piperidinylidene]-5H-imidazo[2,1-b][3]-benzazepine-3-carboxylate (compound 6, mp. 179.3° C.).

EXAMPLE B.7

A mixture of compound 6 (37 g) in NaOH (1N, 150 ml), THF (500 ml) and water (500 ml) was stirred at room temperature overnight. The organic solvent was evaporated. The aqueous concentrate was washed with DCM and acidified with HCl (1N, 150 ml). The solvent was evaporated. The residue was stirred in water, filtered off and dried, yielding 32 g (84%) of 6,11-dihydro-11-[1-[2-[4-(2-quinolinylmethoxy)phenyl]ethyl]-4-piperidinylidene]-5H-imidazo[2,1-b][3]benzazepine-3-carboxylic acid (compound 7, mp. 174.2° C.).

EXAMPLE B.8

A mixture of compound 27 (3.5 g) in methanol (100 ml) was stirred at room temperature. Sodium borohydride (0.34 g) was added portionwise and the mixture was stirred at room temperature for 2 hours. The mixture was evaporated, the residue was taken up in water and extracted with CH$_2$Cl$_2$/C$_2$H$_5$OH. The organic layer was dried, filtered and evaporated. The residue was crystallized from ACN. The precipitate was filtered off and dried, yielding 2.39 g (68%) of (±)-6,10-dihydro-10-[1-[2-[4-(2-quinolinylmethoxy)-phenyl]ethyl]-4-piperidinylidene]-5H-imidazo[1,2-a]-thieno[3,2-d]azepin-6-ol (compound 28, mp. 242.1° C.).

EXAMPLE B.9

A mixture of compound 7 (3 g) and N,N-dimethyl-4-pyridinamine (1.22 g) in DCM (100 ml) was stirred till complete dissolution. 1-(3-Dimethylaminopropyl)-3-ethyl-carbodiimide hydrochloride (1.8 g) was added portionwise and the mixture was stirred at room temperature for 15 minutes. A solution of benzenemethanol (0.54 g) in DCM was added. The mixture was stirred at room temperature overnight. The solvent was evaporated. The residue was purified over silica gel on a glass filter (eluent: CH$_2$Cl$_2$/CH$_3$OH 97/3 to 95/5). The pure fractions were collected and the solvent was evaporated. The residue was crystallized from ACN. The precipitate was filtered off and dried, yielding 2.06 g (62%) of phenylmethyl 6,11-dihydro-11-[1-[2-[4-(2-quinolinylmethoxy)phenyl]ethyl]-4-piperidinylidene]-5H-imidazo[2,1-b][3]benzazepine-3-carboxylate (compound 9). In a similar way, but replacing the alcohol by ammonia or dimethylamine, compound 55 (compound ) and compound 56 (compound) respectively were synthesized.

EXAMPLE B.10

A mixture of compound 2 (27.8 g) in DCM (500 ml) was stirred at room temperature till complete dissolution. Dibenzoylperoxide (a few crystals) was added portionwise, then a solution of N-chlorosuccinimide (7 g) in DCM was added dropwise at room temperature and the mixture was stirred at room temperature for 18 hours. The solvent was evaporated and the residue was purified by column chromatography over silica gel (eluent: $CH_2Cl_2/(CH_3OH/NH_3)$ 96/4 to 92/8). The pure fractions were collected and the solvent was evaporated. The residue was purified further by HPLC over silica gel (eluent: $CH_2Cl_2/CH_3OH$ 96/4 to 50/50). The pure fractions were collected and the solvent was evaporated. The first fraction was crystallized from $CH_3OH$, yielding 8.84 g (30%) of compound 59. The second fraction was crystallized from ACN, yielding 1.91 g (6%) of compound 58.

EXAMPLE B.11

A mixture of compound 6 (5.55 g) and methyl (triphenylphosphoranylidene)acetate (3.34 g) in toluene (300 ml) was stirred and refluxed overnight. The solvent was evaporated. The residue was purified over silica gel on a glass filter (eluent: $CH_2Cl_2/CH_3OH$ 95/5). The pure fractions were collected and the solvent was evaporated. The residue was crystallized from ACN. The precipitate was filtered off, dried, recrystallized from ACN and purified by HPLC Hypersil RP-18 3$\mu$M (eluent: ($NH_4OAc$/0.5% in $H_2O$)/$CH_3OH$/$CH_3CN$ 70/15/15, 0/50/50 to 0/0/100). The pure fractions were collected, evaporated till aqueous and extracted with DCM. The organic layer was separated, dried, filtered and the solvent was evaporated. The residue was crystallized from ACN. The precipitate was filtered off and dried, yielding 0.45 g (7%) of compound 62.

EXAMPLE B.12

A mixture of compound 71 (4.5 g) in $CH_3OH$ (350 ml) was stirred on an ice bath. $NaBH_4$ (0.38 g) was added portionwise at 0° C. over a period of 15 minutes. The mixture was stirred at room temperature for 1 hour and then decomposed with water. The organic solvent, was evaporated. The aqueous concentrate was extracted with DCM. The combined organic layer was dried, filtered and the solvent was evaporated. The residue was purified over silica gel on a glass filter (eluent: $CH_2Cl_2/CH_3OH$ 95/5). The pure fractions were collected and the solvent was evaporated. The residue was crystallized from ACN. The precipitate was filtered off and dried, yielding: 3.5 g (78%) of compound 73.

EXAMPLE B.13

A mixture of methyl 6,11-dihydro-4-piperidinylidene-5H-imidazo[2,1-b][3]benzazepine-3-carboxylate (3.23 g) and N,N-dimethyl pyridinamine (2.4 g) in DCM (200 ml) was stirred at room temperature. 1-(3-Dimethylaminopropyl)-3-ethyl-carbodiimide hydrochloride (3.83 g) was added portionwise. The mixture was stirred at room temperature for 1 hour. 4-(2-Quinolinylmethoxy) benzoic acid (2.8 g) dissolved in DCM was added dropwise. The mixture was stirred at room temperature overnight. Water was added. The mixture was separated into its layers. The aqueous layer was extracted with DCM. The combined organic layer was dried, filtered and the solvent was evaporated. The residue was purified by column chromatography over silica gel (eluent: $CH_2Cl_2/CH_3OH$ 95/5). The pure fractions were collected and the solvent was evaporated. The residue was dissolved in $CH_3OH$ and converted into the (E)-2-butenedioic acid salt (1:1). The precipitate was filtered off and dried, yielding 3.36 g (48%) of compound 72.

EXAMPLE B.14

A mixture of compound 71 (4.5 g) and hydroxylamine (1.1 g) in pyridine (50 ml) was stirred and refluxed for 90 minutes. The solvent was evaporated. The residue was stirred in $H_2O/CH_2Cl_2$. $K_2CO_3$ (2 g) was added. The mixture was separated into its layers. The aqueous layer was extracted with DCM. The combined organic layer was dried, filtered and the solvent was evaporated. The residue was purified over silica gel on a glass filter (eluent: $CH_2Cl_2/CH_3OH$ 95/5). The pure fractions were collected and the solvent was evaporated. The residue was crystallized from ACN. The precipitate was filtered off and dried, yielding 1.21 g (26%) of compound 74.

EXAMPLE B.15

A mixture of 4-phenoxy benzaldehyde (2 g) and methyl 6,11-dihydro-4-piperidinylidene-5H-imidazo[2,1-b][3]benzazepine-3-carboxylate (3.23 g) in methanol (150 ml) was hydrogenated at room temperature overnight with Pd/C (10%, 1 g) as a catalyst in the presence of a thiophene solution (1 ml). After uptake of hydrogen (1 equivalent), the catalyst was filtered off and the filtrate was evaporated. The residue was purified over silica gel on a glass filter (eluent: $CH_2Cl_2/CH_3OH$ 97/3 to 95/5). The pure fractions were collected and the solvent was evaporated. The residue was crystallized from $CH_3OH$. The precipitate was filtered off and dried, yielding: 2.86 g (57%) of compound 90.

EXAMPLE B.16

A mixture of diisopropanolamine (1.13 g) in TBF was stirred under nitrogen at −78° C. N-Butillithium (2.5 M in hexanes, 4.3 ml) was added portionwise at −70° C. and the mixture was stirred for 15 minutes. 1-(Diethoxymethyl)-1H-imidazole (1.81 g) dissolved in THF was added dropwise at −70° C. and the mixture was stirred at −70° C. for 1 hour. Compound 4 (5.54 g) dissolved in THF was added dropwise at −70° C. and the mixture was stirred at −70° C. for 1 hour. The mixture was brought till room temperature and it was stirred at room temperature overnight. Acetic acid (5 ml) was added and the mixture was stirred at room temperature for 20 minutes. $K_2CO_3$ (5 g) was added and the mixture was evaporated. The residue was taken up in water and DCM and the layers were separated. The aqueous layer was extracted with DCM. The combined organic layers were dried, filtered off and the solvent was evaporated, yielding 6.1 g (97%) of 6,11-dihydro-α-(1H-imidazol-2-yl)-11-[1-[2-[4-(2-quinolinylmethoxy)phenyl]ethyl]-4-piperidinylidene]-5H-imidazo[2,1-b][3]benzazepine-3-methanol (compound 46).

Tables F-1 to F-6 list the compounds that were prepared according to one of the above Examples and Table F-7 lists both the experimental (column heading "exp.") and theoretical (column heading "theor.") elemental analysis values for carbon, hydrogen and nitrogen of the compounds as prepared in the experimental part hereinabove.

TABLE F-1

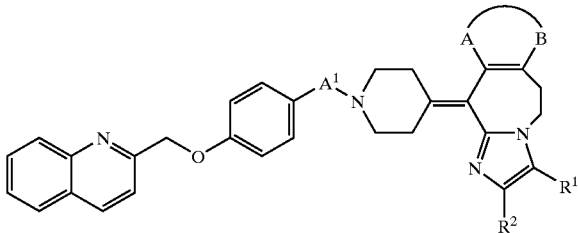

| Co. No. | Ex. No. | A$^1$ | R$^1$ | R$^2$ | —A—B— | Phys. Data (mp. in ° C.) |
|---|---|---|---|---|---|---|
| 14 | B.1 | —(CH$_2$)$_2$— | H | —CH$_3$ | —CH=CH—N(CH$_3$)— | mp. 150 |
| 15 | B.1 | —CH$_2$— | H | H | —CH=CH—N(CH$_3$)— | mp. 199.8 |
| 16 | B.1 | —(CH$_2$)$_2$— | H | H | —CH=CH—N(CH$_3$)— | mp. 179.5 |
| 17 | B.1 | —(CH$_2$)$_2$— | H | H | —CH=CH—CF=CH— | mp. 190.2 |
| 18 | B.1 | —O(CH$_2$)$_2$— | H | H | —CH=CH—N(CH$_3$)— | mp. 174.4 |
| 19 | B.1 | —O(CH$_2$)$_2$— | H | H | —CH=CH—CF=CH— | mp. 136.0 |
| 37 | B.1 | —COCH$_2$— | H | H | —CH=CH—N(CH$_3$)— | mp. 220 |
| 38 | B.12 | —OCH$_2$CHOHCH$_2$— | H | H | —CH=CH—N(CH$_3$)— | mp. 186.4 |
| 39 | B.1 | —(CH$_2$)$_2$— | CH$_2$OH | H | —CH=CH—C(OCH$_3$)=CH— | mp. 106.8 |

TABLE F-2

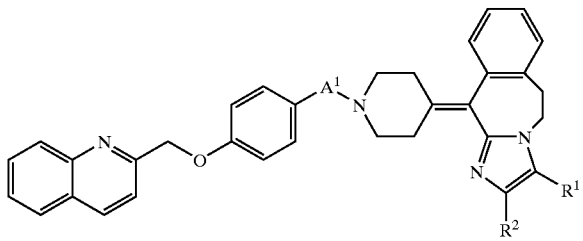

| Co. No. | Ex. No. | A$^1$ | R$^1$ | R$^2$ | Phys. Data (mp. in ° C.) |
|---|---|---|---|---|---|
| 1 | B.1 | —(CH$_2$)$_2$— | H | H | mp. 200.1 |
| 2 | B.1 | —(CH$_2$)$_2$— | —CH$_2$OH | H | mp. 220.1 |
| 3 | B.3 | —(CH$_2$)$_2$— | —CH$_2$OCOCH$_3$ | H | — |
| 4 | B.4 | —(CH$_2$)$_2$— | —CHO | H | mp. 193.5 |
| 5 | B.5 | —(CH$_2$)$_2$— | —CH$_2$COOCH$_3$ | H | — |
| 6 | B.6 | —(CH$_2$)$_2$— | —COOCH$_3$ | H | mp. 179.3 |
| 40 | B.6 | —(CH$_2$)$_2$— | —COOCH$_3$ | H | mp. 142.6; .HCl (1:1).H$_2$O (1:3) |
| 41 | B.6 | —(CH$_2$)$_2$— | —COOCH$_3$ | H | mp. 180.6; .HCl (1:2).H$_2$O (1:1) |
| 42 | B.6 | —(CH$_2$)$_2$— | —COOCH$_3$ | H | mp. 161.8; .(Z)-2-butene-dioate (1:1) |
| 43 | B.6 | —(CH$_2$)$_2$— | —COOCH$_3$ | H | mp. 166.0; .ethanedioate (1:1) |
| 44 | B.6 | —(CH$_2$)$_2$— | —COOCH$_3$ | H | .hydroxybutane-dioate (1:1) |
| 45 | B.6 | —(CH$_2$)$_2$— | —COOCH$_3$ | H | mp. 204.1; .HCl (1:3) |
| 7 | B.7 | —(CH$_2$)$_2$— | —COOH | H | mp. 174.2 |
| 8 | B.1 | —(CH$_2$)$_2$— | —CH$_2$OH | —CH$_2$OH | mp. 183.3; .hemihydrate |
| 9 | B.9 | —(CH$_2$)$_2$— | —COOCH$_2$C$_6$H$_5$ | H | — |
| 10 | B.4 | —(CH$_2$)$_2$— | —CHO | —CHO | — |
| 11 | B.6 | —(CH$_2$)$_2$— | —COOCH$_3$ | —COOCH$_3$ | — |
| 12 | B.6 | —(CH$_2$)$_2$— | —COOC$_2$H$_5$ | H | — |
| 13 | B.1 | —(CH$_2$)$_2$— | Cl | H | — |
| 20 | B.1 | —O(CH$_2$)$_2$— | H | H | mp. 138.2 |
| 46 | B.16 | —(CH$_2$)$_2$— | —CH(OH)-(2-imidazolyl) | H | — |

TABLE F-2-continued

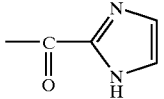

| Co. No. | Ex. No. | A¹ | R¹ | R² | Phys. Data (mp. in ° C.) |
|---|---|---|---|---|---|
| 47 | B.4 | —(CH$_2$)$_2$— | ![imidazole-CO-] | H | mp. 222.6 |
| 48 | B.9 | —(CH$_2$)$_2$— | —COOC$_{10}$H$_{21}$ | H | — |
| 49 | B.9 | —(CH$_2$)$_2$— | —COOC$_{12}$H$_{25}$ | H | — |
| 50 | B.9 | —(CH$_2$)$_2$— | —C(=O)—O—phenyl | H | — |
| 51 | B.9 | —(CH$_2$)$_2$— | —COOCH$_2$-(3,5-dimethylphenyl) | H | — |
| 52 | B.9 | —(CH$_2$)$_2$— | —COOCH$_2$-(5-methylfuran-2-yl) | H | — |
| 53 | B.9 | —(CH$_2$)$_2$— | —COO(CH$_2$)$_2$OC$_2$H$_5$ | H | — |
| 54 | B.9 | —(CH$_2$)$_2$— | —COOCH$_2$-(quinolin-2-yl) | H | — |
| 55 | B.9 | —(CH$_2$)$_2$— | —CONH$_2$ | H | — |
| 56 | B.9 | —(CH$_2$)$_2$— | —CON(CH$_3$)$_2$ | H | — |
| 57 | B.10 | —(CH$_2$)$_2$— | —CH$_2$OH | Cl | mp. 211.3 |
| 58 | B.10 | —(CH$_2$)$_2$— | Cl | Cl | mp. 191.1 |
| 59 | B.10 | —(CH$_2$)$_2$— | Cl | —CH$_2$OH | — |
| 60 | B.4 | —(CH$_2$)$_2$— | Cl | —CHO | — |
| 61 | B.6 | —(CH$_2$)$_2$— | Cl | —COOC$_2$H$_5$ | mp. 173.8 |
| 62 | B.11 | —(CH$_2$)$_2$— | —CH=CH—COOCH$_3$ | H | mp. 172.3 |
| 63 | B.4 | —(CH$_2$)$_2$— | —CHO | Cl | mp. 208.4 |
| 64 | B.1 | —(CH$_2$)$_2$— | H | —CH$_2$OH | mp. 149.0; .(E)-2-butenedioate (1:2) |
| 65 | B.9 | —(CH$_2$)$_2$— | —COO(CH$_2$)$_3$CH$_3$ | H | mp. 130.3 |
| 66 | B.1 | —(CH$_2$)$_2$— | H | —CH$_2$OH | — |
| 67 | B.4 | —(CH$_2$)$_2$— | H | —CHO | mp. 168.9 |
| 68 | B.6 | —(CH$_2$)$_2$— | H | —COOCH$_3$ | mp. 209.9 |
| 69 | B.6 | —(CH$_2$)$_2$— | —COOCH$_3$ | H | mp. 200; .(E)-2-butenedioate (2:3) |
| 70 | B.1 | —CH$_2$— | —COOCH$_3$ | H | mp. 204.3 |
| 71 | B.1 | —COCH$_2$— | —COOCH$_3$ | H | mp. 152.3 |
| 72 | B.13 | —CO— | —COOCH$_3$ | H | mp. 139.7; .(E)-2-butenedioate (1:1) |
| 73 | B.12 | —CH(OH)—CH$_2$— | —COOCH$_3$ | H | mp. 154.9 |
| 74 | B.14 | —C(=NOH)—CH$_2$— | —COOCH$_3$ | H | mp. 186.5 |

TABLE F-2-continued

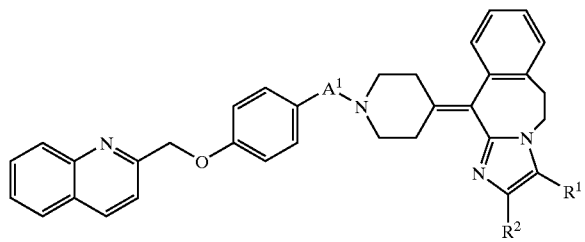

| Co. No. | Ex. No. | A¹ | R¹ | R² | Phys. Data (mp. in ° C.) |
|---|---|---|---|---|---|
| 75 | B.1 | —(CH$_2$)$_3$— | —COOCH$_3$ | H | mp. 156.7 |
| 76 | B.6 | —(CH$_2$)$_2$— | —COOC$_2$H$_5$ | Cl | — |
| 77 | B.9 | —(CH$_2$)$_2$— | —COOCH(CH$_3$)$_2$ | H | mp. 165.9 |
| 102 | B.2 | —CO(CH$_2$)$_3$— | —CH$_2$OH | H | mp. 191.0 |

TABLE F-3

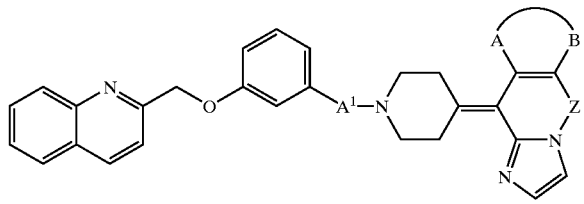

| Co. No. | Ex. No. | A¹ | —A—B— | Z | Physical data (mp. in ° C.) |
|---|---|---|---|---|---|
| 21 | B.1 | —O(CH$_2$)$_2$— | —CH=CH—N(CH$_3$)— | —(CH$_2$)$_2$— | mp. 125.4 |
| 22 | B.1 | —O(CH$_2$)$_2$— | —CH=CH—CF=CH— | —(CH$_2$)$_2$— | mp. 135.6 |
| 23 | B.1 | —(CH$_2$)$_2$— | —CH=CH—CF=CH— | —(CH$_2$)$_2$— | mp. 180; .(cyclohexylsulfamate (1:2) salt |
| 24 | B.1 | —(CH$_2$)$_2$— | —CH=CH—N(CH$_3$)— | —(CH$_2$)$_2$— | mp. 127.7 |
| 25 | B.1 | —(CH$_2$)$_2$— | —CH=CH—S— | —CO—(CH$_2$)*— | mp. 159.9 |
| 78 | B.1 | —(CH$_2$)$_2$— | —CH=CH—CH=CH— | —O—(CH$_2$)*— | mp. 176 |
| 79 | B.1 | —O(CH$_2$)$_2$— | —CH=CH—CH=CH— | —O—(CH$_2$)*— | mp. 189.8 |

*the —CH$_2$— moiety is connected to the nitrogen of the imidazole ring

TABLE F-4

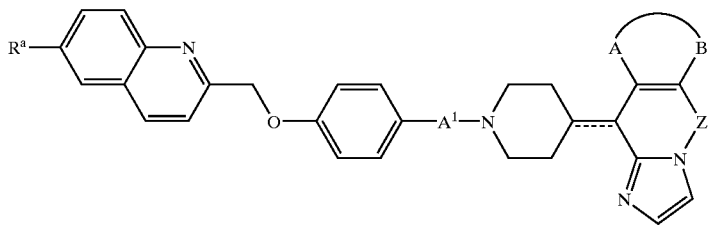

| Co. No. | Ex. No. | R$^a$ | A¹ | ----- | —A—B— | Z | Physical data (mp. in ° C.) |
|---|---|---|---|---|---|---|---|
| 26 | B.1 | H | —O(CH$_2$)$_2$— | double | —CH=CH—S— | —CO—(CH$_2$)*— | mp. 190.5;** |
| 27 | B.1 | H | —(CH$_2$)$_2$— | double | —CH=CH—S— | —CO—(CH$_2$)*— | mp. 201.4 |
| 28 | B.7 | H | —(CH$_2$)$_2$— | double | —CH=CH—S— | —CHOH—(CH$_2$)*— | mp. 242.1 |
| 29 | B.1 | H | —(CH$_2$)$_2$— | single | —CH=CH—N(CH$_3$)— | —CO—(CH$_2$)*— | mp. 200;** |
| 30 | B.1 | H | —(CH$_2$)$_2$— | double | —CH=CH—N(CH$_3$)— | —CO—(CH$_2$)*— | mp. 175.4 |
| 31 | B.1 | —CH$_3$ | —(CH$_2$)$_2$— | double | —CH=CH—N(CH$_3$)— | —(CH$_2$)$_2$— | mp. 188.1 |
| 80 | B.1 | H | —(CH$_2$)$_2$— | double | —CH=CH—CH=CH— | —(CH$_2$)*—O— | mp. 170.7 |

*the —CH$_2$— moiety is connected to the nitrogen of the imidazole ring
**.(E)-2-butenedioate (2:3).ethanolate (1:1) salt form

TABLE F-5

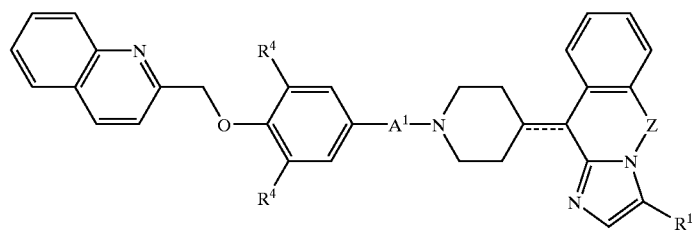

| Co. No. | Ex. No. | $A^1$ | $R^1$ | $R^4$ | ----- | Z | Physical data |
|---|---|---|---|---|---|---|---|
| 32 | B.2 | —CH$_2$— | H | —OCH$_3$ | double | —(CH$_2$)$_2$— | mp. 214.8° C. |
| 33 | B.2 | —CH$_2$— | —CH$_2$OH | —OCH$_3$ | double | —(CH$_2$)$_2$— | mp. 220.8° C. |
| 34 | B.4 | —CH$_2$— | —CHO | —OCH$_3$ | double | —(CH$_2$)$_2$— | mp. 154° C. |
| 35 | B.6 | —CH$_2$— | —COOCH$_3$ | —OCH$_3$ | double | —(CH$_2$)$_2$— | mp. 144.2° C. |
| 36 | B.1 | —(CH$_2$)$_2$ | H | H | single | —CH$_2$— | mp. 169.2° C. |
| 81 | B.1 | —(CH$_2$)$_2$ | —CH$_2$OH | H | single | —(CH$_2$)$_2$— | mp. 179.3° C. |
| 82 | B.4 | —(CH$_2$)$_2$ | —CHO | H | single | —(CH$_2$)$_2$— | mp. 177.8° C. |
| 83 | B.6 | —(CH$_2$)$_2$ | —COOCH$_3$ | H | single | —(CH$_2$)$_2$— | mp. 158.3° C. |
| 84 | B.1 | —(CH$_2$)$_2$ | H | H | double | —CH=CH— | mp. 160.5° C. |
| 85 | B.2 | —CH$_2$— | —COOCH$_3$ | Cl | double | —(CH$_2$)$_2$— | mp. 164.0° C. |
| 86 | B13 | —CO— | —COOCH$_3$ | —CH$_3$ | double | —(CH$_2$)$_2$— | mp. 131.2° C. |

TABLE F-6

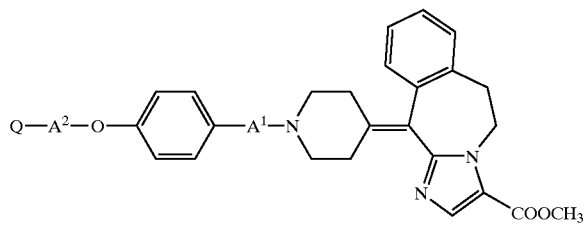

| Co. No. | Ex. No. | Q—A$^2$ | —A$^1$— | Physical data |
|---|---|---|---|---|
| 87 | B.1 | 2-naphthyl-CH$_2$— | —CH$_2$CH$_2$— | — |
| 88 | B.1 | phenylmethyl | —CH$_2$CH$_2$— | — |
| 89 | B.1 | 2-pyridinylmethyl | —CH$_2$CH$_2$— | — |
| 90 | B15 | phenyl | —CH$_2$— | — |
| 91 | B.1 | 1-naphthyl-CH$_2$— | —CH$_2$CH$_2$— | — |
| 92 | B.1 | phenyl-(CH$_2$)$_2$— | —CH$_2$CH$_2$— | — |
| 93 | B.1 | 3,5-bis(trifluromethyl)phenylmethyl | —CH$_2$CH$_2$— | — |
| 94 | B.1 | 1-methyl-2-oxo-1,2-dihydroquinolin-6-yl-CH$_2$— | —CH$_2$CH$_2$— | mp. 190.6° C. |

TABLE F-6-continued

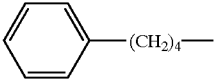

| Co. No. | Ex. No. | Q—A² | —A¹— | Physical data |
|---|---|---|---|---|
| 95 | B.1 | 6-chloro-2-pyridinyl | —CH₂CH₂— | mp. 139.1° C. |
| 96 | B.1 | 4-chlorophenylmethyl | —CH₂CH₂— | mp. 171.2° C. |
| 97 | B.1 | 4-methoxyphenylmethyl | —CH₂CH₂— | mp. 174.8° C. |
| 98 | B.1 | phenyl-(CH₂)₄— | —CH₂CH₂— | mp. 193.5° C.; .(E)-2-butenedioate |
| 99 | B.1 | 3,5-diflurorophenylmethyl | —CH₂CH₂— | mp. 117.2° C. |
| 100 | B.15 | phenyl | —CH₂CH₂— | mp. 132.3° C. |
| 101 | B.1 | 2-quinolinylmethyl | —CH₂O(CH₂)₂— | mp. 125.0 |
| 103 | B.1 | 3,5-dimethylphenylmethyl | —CH₂CH₂— | mp. 123.1 |

TABLE F-7

| Comp. No. | Carbon | | Hydrogen | | Nitrogen | |
|---|---|---|---|---|---|---|
| | Exp. | Theor. | Exp. | Theor. | Exp. | Theor. |
| 3 | 76.00 | 76.23 | 6.42 | 6.40 | 9.30 | 9.36 |
| 5 | 75.28 | 76.23 | 6.35 | 6.40 | 9.18 | 9.36 |
| 9 | 78.08 | 78.16 | 5.97 | 6.10 | 8.44 | 8.48 |
| 11 | 72.77 | 72.88 | 5.76 | 5.96 | 8.71 | 8.72 |
| 12 | 76.12 | 76.23 | 6.33 | 6.40 | 9.41 | 9.36 |
| 13 | 74.81 | 74.92 | 5.78 | 5.93 | 9.88 | 9.98 |
| 76 | 72.62 | 72.08 | 6.09 | 5.89 | 8.84 | 8.85 |
| 87 | 78.24 | 78.19 | 6.31 | 6.39 | 6.85 | 7.20 |
| 88 | 76.32 | 76.52 | 6.63 | 6.61 | 7.73 | 7.87 |
| 89 | 74.02 | 74.13 | 6.45 | 6.41 | 10.50 | 10.48 |
| 90 | 76.22 | 76.02 | 6.35 | 6.18 | 8.35 | 8.31 |
| 91 | 78.85 | 78.19 | 6.42 | 6.39 | 7.10 | 7.20 |
| 92 | 77.57 | 76.76 | 6.86 | 6.81 | 7.62 | 7.67 |
| 93 | 65.05 | 64.57 | 5.14 | 4.97 | 6.14 | 6.27 |

C. Pharmacological Examples

EXAMPLE C-1

The in vitro effectiveness of a compound of formula (I) as a MDR modulator was assessed using a human multidrug resistant cancer cell line (Park J.-G. et al., *J. Natl. Cancer Inst.*, 86:700–705 (1994) and Hill B. T. et al., *Cancer Chemother. Pharmacol.*, 33:317–324 (1994)). Briefly, the cell growth of K562/C1000, a human multidrug resistant cancer cell line, was measured in the presence of a full range of concentrations (ranging from $10^{-12}$ to $10^{-5}$ M) of a classic cytostatic, e.g. vinblastine. The $IC_{50(cytostatic)}$, i.e. the concentration of the cytostatic needed to reduce cell growth by 50%, was measured. Also, the growth of K562/C1000 was measured in the presence of a full range of concentrations of a classic cytostatic and a fixed concentration ($10^{-6}$ M) of a MDR modulating compound, yielding $IC_{50(cytostatic/compound)}$. The sensitization ratio 'SR' is determined as the ratio of $IC_{50(cytostatic)}$ over $IC_{50(cytostatic/compound)}$. Compounds 1, 3, 4, 6, 9, 11–13, 18, 20, 27, 30–36, 47, 45, 58, 61–63, 65, 67, 69, 70, 73, 74, 75, 77, 82, 84, 87–89 and 91–101 as listed in Tables F-1 to F-6 have a SR value greater or equal than 5. Compounds 2, 5, 8, 14, 15, 19, 19, 22, 23–25, 26, 29, 33, 37, 38, 48, 52, 55–57, 64, 68, 71, 76, 78, 79, 80 and 85 as listed in Tables F-1 to F-6 have a SR value between 1 and 5.

EXAMPLE C-2

The potential of compounds of formula (I) to reverse multidrug resistance can be demonstrated by the ability of compounds of formula (I) to reverse the adriamycine resistance in the P388/ADR (adriamycine resistance cell line) murine leukemia in vivo.

Male B6D2F1 mice (18–21 g) were injected intraperitoneally with 1×10⁵ P388/ADR cells at day 0. Daily intraperitoneal treatment with adriamycine, a test compound of formula (I) or a combination of both was installed from day 1 until day 10. Control animals received the vehicle (15% 4-OH-propyl-β-cyclodextrine in saline). Each group consisted of 8 animals. Adriamycine was dosed at a concentration of 1.25 mg/kg body weight, half the maximal tolerable dose of adriamycine in this treatment schedule. The test compound was dosed at 20, 10, 5, 2.5, 1.25 and 0.63 mg/kg either as single treatment or combined with adriamycine.

Survival of the animals was recorded each day and expressed as a percentage of the median survival in the treated groups compared to the median survival in the control group, the latter to be said to be 100%.

Table C-1 lists the effect of compound 6 and adriamycine on the survival of mice injected with P388/ADR leukemia.
- doses of compound 6 and adriamycine are expressed as mg/kg body weight.
- the column "Survival Days" give the median day of death after inoculation of 1×10⁵ P388/ADR cells at day 0, with the minimum and maximum number of days shown in parenthesis. p1 the column "MST%" shows the median percentage of the treated groups compared to the medium survival in the control group, the latter be said to be 100%
- column "% Change vs. ADR" give the difference in MST% of the different groups compared to the MST% in the adriamycine-monotherapy group.

TABLE C-1

| Compound 6 (mg/kg) | Adriamycine (mg/kg) | Survival Days med(min-max) | MST % | % Change vs. ADR |
|---|---|---|---|---|
| 0 | 0 | 11(10–14) | 100 | −18 |
| 0 | 1.25 | 13(12–15) | 118 | 0 |
| 20 | 0 | 11(10–14) | 100 | −18 |
| 10 | 0 | 10.5(10–13) | 95 | −23 |
| 5 | 0 | 11(10–13) | 100 | −18 |
| 2.5 | 0 | 10.5(10–12) | 95 | −23 |
| 1.25 | 0 | 11.5(10–16) | 105 | −13 |
| 0.63 | 0 | 11(10–12) | 100 | −18 |
| 20 | 1.25 | 15.5(14–17) | 141 | 23 |
| 10 | 1.25 | 15(14–28) | 136 | 18 |
| 5 | 1.25 | 14.5(11–16) | 132 | 14 |
| 2.5 | 1.25 | 14.5(10–20) | 132 | 14 |
| 1.25 | 1.25 | 15(14–17) | 136 | 18 |
| 0.63 | 1.25 | 14.5(14–>30) | 132 | 14 |

Table C-1 illustrated that the group treated with a combination of compound 6 and adriamycine have a Median Survival Time (MST) which is 14 to 23% longer than the adriamycine mono-therapy group.

EXAMPLE C-3

The improvement in oral bioavailability was studied using a combination therapy of compound (6) and the anti-neoplastic agent paclitaxel (Taxol®). Mice were treated orally (80 mg/kg po) with compound (6) about 10 to 20 minutes prior to oral administration of taxol (10 mg/kg po). The Area Under the Curve (AUC) was measured and compared with the AUC of mice treated only with taxol. An increase in AUC was measured from 0.82±0.11 to 1.39±0.09 mg/l.hour giving an improvement in the ratio of AUC of 1.7.

What is claimed is:

1. A method for improving the bioavailability of a second pharmaceutical agent in a warm-blooded animal in need thereof wherein the second pharmaceutical agent interacts with a membrane-associated transporter comprising orally co-administering to the warm-blooded animal a first pharmaceutical compound of formula (I)

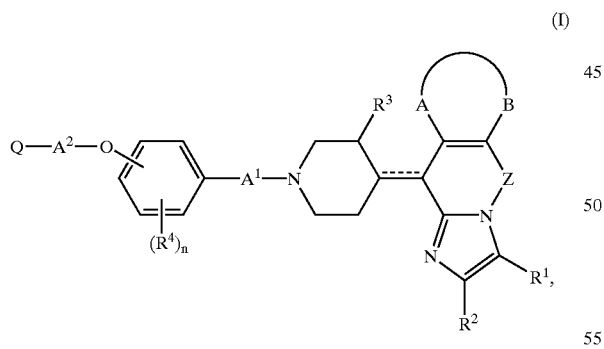

(I)

a N-oxide form, a pharmaceutically acceptable addition salt or a stereochemically isomeric form thereof, wherein
the dotted line represents an optional bond;
n is 1 or 2;
$R^1$ is hydrogen; halo; formyl; $C_{1-4}$alkyl; $C_{1-4}$alkyl substituted with 1 or 2 substituents each independently selected from hydroxy, $C_{1-4}$alkyloxy, $C_{1-4}$alkylcarbonyloxy, imidazolyl, thiazolyl or oxazolyl; or a radical of formula —X—CO—OR$^5$ (a-1);

—X—CO—NR$^6$R$^7$ (a-2);

or

—X—CO—R$^{10}$ (a-3);

wherein
—X— is a direct bond, $C_{1-4}$alkanediyl or $C_{2-6}$alkenediyl;
$R^5$ is hydrogen; $C_{1-12}$alkyl; Ar; Het; $C_{1-6}$alkyl substituted with $C_{1-4}$alkyloxy, $C_{1-4}$alkyloxycarbonyl$C_{1-4}$alkyloxy, Ar or Het;
$R^6$ and $R^7$ each independently are hydrogen or $C_{1-4}$alkyl;
$R^{10}$ is imidazolyl, thiazolyl or oxazolyl;
$R^2$ is hydrogen, halo, $C_{1-4}$alkyl, hydroxy$C_{1-4}$alkyl, $C_{1-4}$alkyloxycarbonyl, carboxyl, formyl or phenyl;
$R^3$ is hydrogen, $C_{1-4}$alkyl or $C_{1-4}$alkyloxy;
$R^4$ is hydrogen, halo, $C_{1-4}$alkyl, $C_{1-4}$alkyloxy or halo$C_{1-4}$alkyl;
Z is $Z^1$ or $Z^2$;
wherein
$Z^1$ is a bivalent radical of formula —$CH_2$—, —$CH_2$—$CH_2$— or —CH=CH—; provided that when the dotted line is a bond, then $Z^1$ is other than —$CH_2$—;
$Z^2$ is a bivalent radical of formula —CHOH—$CH_2$—, —O—$CH_2$—, —C(=O)—$CH_2$— or —C(=NOH)—$CH_2$—;
—A—B— is a bivalent radical of formula —Y—CR$^8$=CH— (b-1);

—CH=CR$^8$—Y— (b-2);

—CH=CR$^8$—CH=CH— (b-3);

—CH=CH—CR$^8$=CH— (b-4);

or

—CH=CH—CH=CR$^8$— (b-5);

wherein
each $R^8$ independently is hydrogen, halo, $C_{1-4}$alkyl, $C_{1-4}$alkyloxy, hydroxy$C_{1-4}$alkyl, hydroxycarbonyl$C_{1-4}$alkyl, formyl, carboxyl, ethenyl substituted with carboxyl, or ethenyl substituted with $C_{1-4}$alkyloxycarbonyl;
each Y independently is a bivalent radical of formula —O—, —S— or —NR$^9$—; wherein $R^9$ is hydrogen, $C_{1-4}$alkyl or $C_{1-4}$alkylcarbonyl;
—$A^1$— is a direct bond; $C_{1-6}$alkanediyl; $C_{1-6}$alkanediyl-oxy-$C_{1-6}$alkanediyl; $C_{1-6}$alkanediyloxy; carbonyl; $C_{1-6}$alkanediylcarbonyl; $C_{1-6}$alkanediyloxy substituted with hydroxy; or $C_{1-6}$alkanediyl substituted with hydroxy or =NOH;
—$A^2$— is a direct bond or $C_{1-6}$alkanediyl;
Q is phenyl; phenyl substituted with one or two substituents selected from hydrogen, halo, hydroxy, $C_{1-4}$alkyl, $C_{1-4}$alkyloxy or halo$C_{1-4}$alkyl; naphthalenyl; naphthalenyl substituted with one or two substituents selected from hydrogen, halo, hydroxy, $C_{1-4}$alkyl, $C_{1-4}$alkyloxy or halo$C_{1-4}$alkyl; pyridinyl; pyridinyl substituted with one or two substituents selected from hydrogen, halo, hydroxy, $C_{1-4}$alkyl, $C_{1-4}$alkyloxy or halo$C_{1-4}$alkyl; quinolinyl; or quinolinyl substituted with one or two substituents selected from hydrogen, halo, hydroxy, $C_{1-4}$alkyl, $C_{1-4}$alkyloxy or halo$C_{1-4}$alkyl;

Ar is phenyl or phenyl substituted with 1, 2 or 3 substituents each independently selected from hydrogen, halo, $C_{1-4}$alkyl or $C_{1-4}$alkyloxy;

Het is furanyl; furanyl substituted with $C_{1-4}$alkyl, $C_{1-4}$alkyloxy or hydroxy$C_{1-4}$alkyl; oxazolyl; oxazolyl substituted with $C_{1-4}$alkyl or $C_{1-4}$alkyloxy; or quinolinyl.

2. The method of claim 1 of a first pharmaceutical compound of formula (I) wherein Z is —CH$_2$—CH$_2$—; —A—B— is —CH=CH—CH=CH—; —A$^1$— is —CH$_2$—CH$_2$——CH$_2$—CH$_2$—CH$_2$— or —O—CH$_2$—CH$_2$—; —A$^2$— is —CH$_2$—; R$^1$ is hydrogen, halo, formyl or a radical of formula (a-1) wherein X is a direct bond and R$^5$ is hydrogen, $C_{1-12}$alkyl, Ar or $C_{1-6}$alkyl substituted with Het; R$^2$ is hydrogen, $C_{1-4}$alkyl, formyl or $C_{1-4}$alkyloxycarbonyl; R$^3$ is hydrogen; R$^4$ is hydrogen or $C_{1-4}$alkyloxy and the dotted line represents a bond.

3. The method of claim 1 wherein the first pharmaceutical compound of formula (I) is methyl 6,11-dihydro-11-[1-[2-[4-(2-quinolinylmethoxy)phenyl]ethyl]4-piperidinylidene]-5H-imidazo[2,1-b][3]benzazepine-3-carboxylate; or a stereoisomeric form or a pharmaceutically acceptable addition salts thereof.

4. The method of claim 1 wherein the second pharmaceutical agent is an antitumor or antineoplastic agent.

5. Use according to claim 4 wherein the second pharmaceutical agent is selected from the group consisting of paclitaxel, docetaxel, other related taxanes, adriamycine, cladribine, cisplatin, cyclophosphamide, dactinomycin, daunorubicin, doxorubicin, etoposide, finasteride, 5-fluorouracil, irinotecan, leucovorin, mitomycin, mitoxantrone, tamoxifen, topotecan, trimetrexate, vincristine, vinblastine, and the pharmaceutically acceptable salts and derivatives thereof.

6. The method of claim 1 wherein the first pharmaceutical compound of formula (I) and the second pharmaceutical agent are each administered in separate oral dosage forms.

7. The method of claim 1 wherein the first pharmaceutical compound of formula (I) and the second pharmaceutical agent are administered together in a combination oral dosage form.

8. The method of claim 1 wherein the first pharmaceutical compound of formula (I) and the second pharmaceutical agent are co-administered in such a way that both are present in the gut lumen and/or membranes during at least partially overlapping times.

9. The method of claim 1 wherein the first pharmaceutical compound of formula (I) is administered either
   a) about 0.5 to 24 hours before, or
   b) less than 30 minutes before, together with or less than 30 minutes after, the administration of the second pharmaceutical agent.

10. The method of claim 1 wherein the second pharmaceutical agent is suitable in the treatment of diseases selected from the group consisting of haematological tumors (leukemias, lymphomas), renal carcinoma, melanoma, ovarian cancer, breast cancer, lung cancer, head and neck carcinomas, hepatocellular carcinoma, liver metastases, genito-urinary and gastrointestinal tract cancers and Kaposi's sarcoma.

* * * * *